United States Patent
Copik et al.

(10) Patent No.: US 12,070,474 B2
(45) Date of Patent: Aug. 27, 2024

(54) METHODS AND COMPOSITIONS FOR NATURAL KILLER CELLS

(71) Applicant: UNIVERSITY OF CENTRAL FLORIDA RESEARCH FOUNDATION, INC., Orlando, FL (US)

(72) Inventors: Alicja J. Copik, Orlando, FL (US); Jeremiah L. Oyer, Orlando, FL (US); Robert Y. Igarashi, Orlando, FL (US); Deborah Altomare, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 283 days.

(21) Appl. No.: 17/585,126

(22) Filed: Jan. 26, 2022

(65) Prior Publication Data

US 2022/0143092 A1 May 12, 2022

Related U.S. Application Data

(62) Division of application No. 15/522,361, filed as application No. PCT/US2015/057591 on Oct. 27, 2015, now Pat. No. 11,260,076.

(60) Provisional application No. 62/069,057, filed on Oct. 27, 2014.

(51) Int. Cl.

| | |
|---|---|
| *A61K 38/20* | (2006.01) |
| *A61K 35/13* | (2015.01) |
| *A61K 35/17* | (2015.01) |
| *A61K 38/17* | (2006.01) |
| *C07K 14/54* | (2006.01) |
| *C07K 14/55* | (2006.01) |
| *C07K 14/705* | (2006.01) |
| *C12N 5/0783* | (2010.01) |
| *A61K 35/12* | (2015.01) |

(52) U.S. Cl.
CPC ............ *A61K 35/17* (2013.01); *A61K 35/13* (2013.01); *A61K 38/177* (2013.01); *A61K 38/20* (2013.01); *A61K 38/2013* (2013.01); *C07K 14/54* (2013.01); *C07K 14/5434* (2013.01); *C07K 14/55* (2013.01); *C07K 14/70525* (2013.01); *C07K 14/70596* (2013.01); *C12N 5/0646* (2013.01); *A61K 2035/124* (2013.01); *C12N 2500/84* (2013.01); *C12N 2501/2302* (2013.01); *C12N 2501/2321* (2013.01); *C12N 2501/599* (2013.01)

(58) Field of Classification Search
CPC .................................................. A61K 38/20
See application file for complete search history.

(56) References Cited

U.S. PATENT DOCUMENTS

| | | |
|---|---|---|
| 6,849,452 B1 | 2/2005 | Zitvogel |
| 7,435,596 B2 | 10/2008 | Campana et al. |
| 8,026,097 B2 | 9/2011 | Campana et al. |
| 2010/0111916 A1 | 5/2010 | Xiang |
| 2013/0058921 A1 | 3/2013 | Van Rhee |
| 2013/0266551 A1 | 10/2013 | Campana et al. |
| 2015/0190471 A1 | 7/2015 | Copik |

FOREIGN PATENT DOCUMENTS

| | | |
|---|---|---|
| CN | 102559600 A | 7/2012 |
| CN | 102911918 A | 2/2013 |
| CN | 103232973 A | 8/2013 |
| CN | 103484429 A | 1/2014 |
| WO | 03011330 A1 | 2/2003 |
| WO | 2014005072 A1 | 1/2014 |
| WO | 2014089029 A1 | 6/2014 |

OTHER PUBLICATIONS

Alici, E., T. Sutlu, et al. (2008). "Autologous antitumor activity by NK cells expanded from myeloma patients using GMP-compliant components." Blood 111(6): 3155-3162.
Andreev, O. A., A. D. Dupuy, et al. (2007). "Mechanism and uses of a membrane peptide that targets tumors and other acidic tissues in vivo." Proc Natl Acad Sci U S A 104(19): 7893-7898.
Baker, K. S., S. M. Davies, et al. (2009). "Race and socioeconomic status influence outcomes of unrelated donor hematopoietic cell transplantation." Biol Blood Marrow Transplant 15(12): 1543-1554.
Berg, M. and R. Childs (2010). "Ex-vivo expansion of NK cells: what is the priority—high yield or high purity?" Cytotherapy 12(8): 969-970.
Berg, M., A. Lundqvist, et al. (2009). "Clinical-grade ex vivo-expanded human natural killer cells up-regulate activating receptors and death receptor ligands and have enhanced cytolytic activity against tumor cells." Cytotherapy 11(3): 341-355.
Bottino, C., R. Castriconi, et al. (2005). "Cellular ligands of activating NK receptors." Trends Immunol 26(4): 221-226.
Bryceson, Y. T., H. G. Ljunggren, et al. (2009). "Minimal requirement for induction of natural cytotoxicity and intersection of activation signals by inhibitory receptors." Blood 114(13): 2657-2666.
Carlens, S., M. Gilljam, et al. (2001). "A new method for in vitro expansion of cytotoxic human CD3-CD56+ natural killer cells." Hum Immunol 62(10): 1092-1098.
Chaput et al., (2005). The potential of exosomes in immunotherapy of cancer, Blood Cells, Molecules, & Diseases 35(2), 111-115.
Chitadze et al., (2013). Generation of Soluble NKG2D Ligands: Proteolytic Cleavage, Exosome Secretion and Functional Implications, Scandinavian Journal of Immunology, 78(2), 120-129.

(Continued)

*Primary Examiner* — Prema M Mertz
(74) *Attorney, Agent, or Firm* — Meunier Carlin & Curfman LLC

(57) ABSTRACT

Disclosed herein are novel compositions and methods for stimulation of and the production or expansion of natural killer (NK) cells. Numbers of NK cells can be increased following contact with exosomes modified with one or more stimulatory peptides. Methods and compositions for the production of exosomes, wherein the exosomes comprises stimulatory peptides are also described. Also described are methods of treating cancer using the disclosed NK-stimulating exosomes or NK cells stimulated by the disclosed methods.

12 Claims, 6 Drawing Sheets

(56) References Cited

OTHER PUBLICATIONS

Cho, D. and D. Campana (2009). "Expansion and activation of natural killer cells for cancer immunotherapy." Korean J Lab Med 29(2): 89-96.
Cho, D., D. R. Shook, et al. (2010). "Cytotoxicity of activated natural killer cells against pediatric solid tumors." Clin Cancer Res 16(15): 3901-3909.
Denman, C. J., V. V. Senyukov, et al. (2012). "Membrane-bound IL-21 promotes sustained ex vivo proliferation of human natural killer cells." PLoS One 7(1): e30264.
Dewan, M. Z., M. Takada, et al. (2009). "Natural killer activity of peripheral-blood mononuclear cells in breast cancer patients." Biomed Pharmacother 63(9): 703-706.
Drobyski, W. R., J. Klein, et al. (2002). "Superior survival associated with transplantation of matched unrelated versus one-antigen-mismatched unrelated or highly human leukocyte antigen-disparate haploidentical family donor marrow grafts for the treatment of hematologic malignancies: establishing a treatment algorithm for recipients of alternative donor grafts." Blood 99(3): 806-814.
Dunbar, E. M., M. P. Buzzeo, et al. (2008). "The relationship between circulating natural killer cells after reduced intensity conditioning hematopoietic stem cell transplantation and relapse-free survival and graft-versus-host disease." Haematologica 93(12): 1852-1858.
Elsner et al., (2007). The Heat Shock Protein HSP70 Promotes Mouse NK Cell Activity against Tumors That Express Inducible NKG2D Ligands, Journal of Immunology, 179(8), 5523-5533.
Fujisaki, H., H. Kakuda, et al. (2009). "Expansion of highly cytotoxic human natural killer cells for cancer cell therapy." Cancer Res 69(9): 4010-4017.
Gasser, S., S. Orsulic, et al. (2005). "The DNA damage pathway regulates innate immune system ligands of the NKG2D receptor." Nature 436(7054): 1186-1190.
Gastpar et al., (2005). Heat Shock Protein 70 Surface-Positive Tumor Exosomes Stimulate Migratory and Cytolytic Activity of Natural Killer Cells, Cancer Research 65(12), 5238-5247.
Gehrmann et al., (2014). Harnessing the exosome-induced immune response for cancer immunotherapy, Seminars in Cancer Biology, DOI:10.1016/j.semcancer.2014.05.003.
Geller, M. A., S. Cooley, et al. (2011). "A phase II study of allogeneic natural killer cell therapy to treat patients with recurrent ovarian and breast cancer." Cytotherapy 13(1): 98-107.
Harada, H., K. Saijo, et al. (2002). "Selective expansion of human natural killer cells from peripheral blood mononuclear cells by the cell line, HFWT." Jpn J Cancer Res 93(3): 313-319.
Harada, H., K. Saijo, et al. (2004). "A GFP-transfected HFWT cell line, GHINK-1, as a novel target for non-RI activated natural killer cytotoxicity assay." Hum Cell 17(1): 43-48.
Hatjiharissi, E., L. Xu, et al. (2007). "Increased natural killer cell expression of CD16, augmented binding and ADCC activity to rituximab among individuals expressing the Fc{ gamma } RIIIa-158 V/V and V/F polymorphism." Blood 110(7): 2561-2564.
Henslee-Downey, P. J., S. H. Abhyankar, et al. (1997). "Use of partially mismatched related donors extends access to allogeneic marrow transplant." Blood 89(10): 3864-3872.
Hong Chang Sook et al., (2014). "Isolation and Characterization of CD34+ Blast-Derived Exosomes in Acute Myeloid Leukemia", PloS one, 9(8), e103310.
Hong Chang-Sook et al., (2014). "Plasma exosomes as markers of therapeutic response in patients with acute myeloid leukemia", From Frontiers in immunology, 5160.
Houot, R., H. E. Kohrt, et al. (2011). "Targeting immune effector cells to promote antibody-induced cytotoxicity in cancer immunotherapy." Trends Immunol 32(11): 510-516.
Hunt, J. F., P. Rath, et al. (1997). "Spontaneous, pH-dependent membrane insertion of a transbilayer alpha-helix." Biochemistry 36(49): 15177-15192.

Imai, C., S. Iwamoto, et al. (2005). "Genetic modification of primary natural killer cells overcomes inhibitory signals and induces specific killing of leukemic cells." Blood 106(1): 376-383.
Keller, Sascha, et al., (2009). Systemic presence and tumor-growth promoting effect of ovarian carcinoma released exosomes, Cancer Letters (Shannon, Ireland) 278(1), 73-81.
Kim et al., (1993) "The use of palmitate-conjugated protein A for coating cells with artificial receptors which facilitate intercellular interactions", Journal of Immunological Methods, 158(1):57-65.
Kueng, H. J., V. M. Leb, et al. (2007). "General strategy for decoration of enveloped viruses with functionally active lipid-modified cytokines." J Virol 81(16): 8666-8676.
Kuerer, H. M., A. U. Buzdar, et al. (2011). "Biologic and immunologic effects of preoperative trastuzumab for ductal carcinoma in situ of the breast." Cancer 117(1): 39-47.
Kute, T. E., L. Savage, et al. (2009). "Breast tumor cells isolated from in vitro resistance to trastuzumab remain sensitive to trastuzumab anti-tumor effects in vivo and to ADCC killing." Cancer Immunol Immunother 58(11): 1887-1896.
Lee, D. A., M. R. Verneris, et al. (2010). "Acquisition, preparation, and functional assessment of human NK cells for adoptive immunotherapy." Methods Mol Biol 651: 61-77.
Liu, S., D. R. Breiter, et al. (2007). "Enhanced antitumor responses elicited by combinatorial protein transfer of chemotactic and costimulatory molecules." J Immunol 178(5): 3301-3306.
Ljunggren, H. G. and K. J. Malmberg (2007). "Prospects for the use of NK cells in immunotherapy of human cancer." Nat Rev Immunol 7(5): 329-339.
Lugini et al., (2012), "Immune Surveillance Properties of Human NK Cell-Derived Exosomes", Journal of Immunology 189(6), 2833-2842.
Lv, Li-Hong et al., "Anticancer Drugs Cause Release of Exosomes with Heat Shock Proteins from Human Hepatocellular Carcinoma Cells That Elicit Effective Natural Killer Cell Antitumor Responses in Vitro", Journal of Biological Chemistry (2012), 287(19), 15874-15885.
Mamessier, E., A. Sylvain, et al. (2011). "Human breast cancer cells enhance self tolerance by promoting evasion from NK cell antitumor immunity." J Clin Invest 121(9): 3609-3622.
Marcus, et al., (2009), "FedExosomes: Engineering Therapeutic Biological Nanoparticles that Truly Deliver", Pharmaceuticals 6(5): 659-680.
Miller, J. S. (2009). "Should natural killer cells be expanded in vivo or ex vivo to maximize their therapeutic potential?" Cytotherapy 11(3): 259-260.
Miller, J. S., Y. Soignier, et al. (2005). "Successful adoptive transfer and in vivo expansion of human haploidentical NK cells in patients with cancer." Blood 105(8): 3051-3057.
Morse et al., (2005). "A phase I study of dexosome immunotherapy in patients with advanced non-small cell lung cancer", Journal of Translational Medicine 3, No pp. given. DOI:10.1186/1479-5876-3-9.
Paulick, M. G., A. R. Wise, et al. (2007). "Synthetic analogues of glycosylphosphatidylinositol-anchored proteins and their behavior in supported lipid bilayers." J Am Chem Soc 129(37): 11543-11550.
Paulick, M. G., M. B. Forstner, et al. (2007). "A chemical approach to unraveling the biological function of the glycosylphosphatidylinositol anchor." Proc Natl Acad Sci U S A 104(51): 20332-20337.
International Search Report and Written Opinion issued in Application No. PCT/US15/57591, dated Jan. 27, 2016.
International Preliminary Report on Patentability issued in Application No. PCT/US15/57591, dated May 11, 2017.
Reim, F., Y. Dombrowski, et al. (2009). "Immunoselection of breast and ovarian cancer cells with trastuzumab and natural killer cells: selective escape of CD44high/CD24low/HER2low breast cancer stem cells." Cancer Res 69(20): 8058-8066.
Reiners Katrin S., (2014). "Role of Exosomes Released by Dendritic Cells and/or by Tumor Targets: Regulation of NK Cell Plasticity", Frontiers in immunology, 591.
Reshetnyak, Y. K., M. Segala, et al. (2007). "A monomeric membrane peptide that lives in three worlds: in solution, attached to, and inserted across lipid bilayers." Biophys J 93(7): 2363-2372.
Reshetnyak, Y. K., O. A. Andreev, et al. (2006). "Translocation of molecules into cells by pH-dependent insertion of a transmembrane helix." Proc Natl Acad Sci U S A 103(17): 6460-6465.

(56) References Cited

OTHER PUBLICATIONS

Rubnitz, J. E., H. Inaba, et al. (2010). "NKAML: a pilot study to determine the safety and feasibility of haploidentical natural killer cell transplantation in childhood acute myeloid leukemia." J Clin Oncol 28(6): 955-959.
Ruggeri, L., M. Capanni, et al. (2002). "Effectiveness of donor natural killer cell alloreactivity in mismatched hematopoietic transplants." Science 295(5562): 2097-2100.
Siegler, U., S. Meyer-Monard, et al. (2010). "Good manufacturing practice-compliant cell sorting and large-scale expansion of single KIR-positive alloreactive human natural killer cells for multiple infusions to leukemia patients." Cytotherapy 12:6, 750-763.
Somanchi, S. S., V. V. Senyukov, et al. (2011). "Expansion, purification, and functional assessment of human peripheral blood NK cells." J Vis Exp(48).
Stephan Munich, et al., Dendritic cell exosomes directly kill tumor cells and activate natural killer cells via TNF superfamily ligands, OncoImmunology 1:7, 1074-1083.
Suck, G. and M. B. Koh (2010). "Emerging natural killer cell immunotherapies: large-scale ex vivo production of highly potent anticancer effectors." Hematol Oncol Stem Cell Ther 3(3): 135-142.
Tai, Y. T., H. M. Horton, et al. (2012). "Potent in vitro and in vivo activity of an Fc- engineered humanized anti-HM1.24 antibody against multiple myeloma via augmented effector function." Blood 119(9): 2074-2082.
Triulzi, C., S. Vertuani, et al. (2010). "Antibody-dependent natural killer cell-mediated cytotoxicity engendered by a kinase-inactive human HER2 adenovirus-based vaccination mediates resistance to breast tumors." Cancer Res 70(19): 7431-7441.
Viaud, S., M. Terme, et al. (2009). "Dendritic cell-derived exosomes promote natural killer cell activation and proliferation: a role for NKG2D ligands and IL-15Ralpha." PLoS One 4(3): e4942.
Wang et al., (2014), "Good things come in small packages: exosomes, immunity and cancer", Cancer Gene Therapy 21(4), 139-141.
Whiteside, et al., (2013), "Immune modulation of T-cell and NK (natural killer) cell activities by TEXs (tumour-derived exosomes)", Biochem Soc Trans 41(1), 245-51.
Woan, K. and V. Reddy (2007). "Potential therapeutic role of natural killer cells in cancer." Expert Opin Biol Ther 7(1): 17-29.
Yamauchi, C., S. Fujii, et al. (2011). "E-cadherin expression on human carcinoma cell affects trastuzumab-mediated antibody-dependent cellular cytotoxicity through killer cell lectin-like receptor G1 on natural killer cells." Int J Cancer 128(9): 2125-2137.
Yang Yunshan et al., (2013). "Increased induction of antitumor response by exosomes derived from interleukin-2 gene-modified tumor cells", Journal of cancer research and clinical oncology, 133(6), 389-99.
Zech et al., (2012). Tumor-exosomes and leukocyte activation: an ambivalent crosstalk, Cell Communication and Signaling 10, 37, Caplus, DOI:10.1186/1478-811X-10-37.
Extended European Search Report in Application No. EP15853854. 6, dated Mar. 29, 2018, 7 pages.
J.M. Pitt et al., "Dendritic Cell-Derived Exosomes as Immunotherapies in the Fight Against Cancer", The Journal of Immunology, vol. 193, No. 3, Jul. 21, 2014, pp. 1006-1011.
Clayton et al., Human Tumor-Derived Exosomes Selectively Impair Lymphocyte Responses to Interleukin-2, Cancer Res 2007; 67: (15). Aug. 1, 2007, pp. 7458-7466.
Singh et al., Reprogramming CD19-Specific T Cells with IL-21 Signaling Can Improve Adoptive Immunotherapy of B-Lineage Malignancies, Cancer Res; 71(10), May 15, 2011, 3516-27.
Written Opinion issued Dec. 15, 2019 for Singaporean Application No. 11201703397U.
English Translation of Office Action issued Dec. 26, 2019, for Chinese Application No. 201580071084.0.
Communication pursuant to Article 94(3) EPC issued by the European Patent office for Application No. 15853854.6 dated Jul. 22, 2020.
English Translation of Office Action issued Jul. 24, 2020, for Chinese Application No. 201580071084.0.
First Examination Report for Australian Application No. 2015339447 dated Aug. 4, 2020.
English translation of Notice of Reasons for Rejection for Japanese Application No. 2017-522656 dated Sep. 15, 2020.
English translation of Notice of Reasons for Rejection for Japanese Application No. 2017-522656 dated Nov. 5, 2019.
Segura, et al., Blood, 2005, vol. 106, No. 1, p. 216-223.
Marcus, et al., Pharmaceuticals, 2013, vol. 6, p. 659-680.
Seo, Drug Delivery System, Mar. 25, 2014, vol. 29, pp. 152-159.
Communication Pursuant to Article 94(3) EPC, issued for Application No. 15853854.6, dated Jun. 8, 2021.
Gong, W., et al. "Ex vivo expansion of natural killer cells with high cytotoxicity by K562 cells modified to co-express major histocompatibility complex class I chain-related protein A, 4-1BB ligand, and interleukin-15." Tissue antigens 76.6 (2010): 467-475.
Savina, Ariel, Michel Vidal, and Maria I. Colombo. "The exosome pathway in K562 cells is regulated by Rab11." Journal of cell science 115.12 (2002): 2505-2515.
Goodwin, Raymond G., et al. "Molecular cloning of a ligand for the inducible T cell gene 4-1BB: a member of an emerging family of cytokines with homology to tumor necrosis factor." European journal of immunology 23.10 (1993): 2631-2641.
Le Pecq, Jean-Bernard. "Dexosomes as a therapeutic cancer vaccine: from bench to bedside." Blood Cells, Molecules, and Diseases 35.2 (2005): 129-135.
Yao, Ye, et al. "Dendritic cells pulsed with leukemia cell-derived exosomes more efficiently induce antileukemic immunities." PloS one 9.3 (2014): e91463.
English translation of Japanese Office Action issued in JP 2021-193325, mailed Jul. 5, 2023.
English translation of Brazilian Office Action issued in BR112017008696-4, mailed Jun. 4, 2023.
English translation of Chinese Office Action issued in CN202110106858. 6, mailed Jul. 29, 2023.

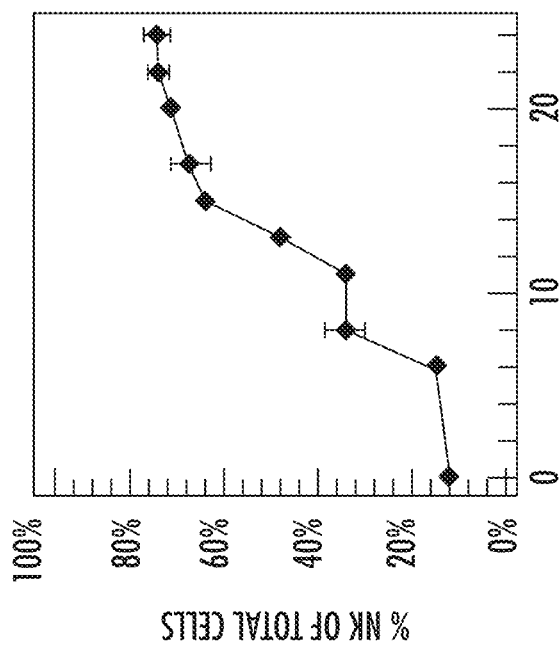
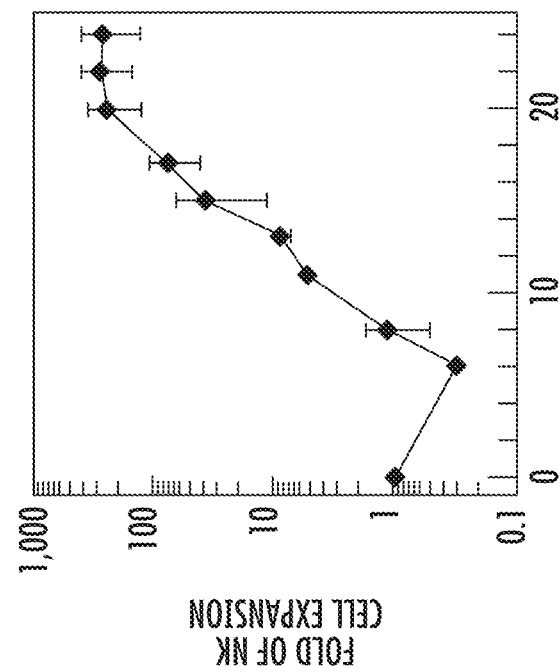
FIG. 3A
FIG. 3B

METHODS AND COMPOSITIONS FOR NATURAL KILLER CELLS

CROSS-REFERENCE TO RELATED APPLICATIONS

This application is a division of U.S. patent application Ser. No. 15/522,361, filed Apr. 27, 2017, which is a national stage application filed under 35 U.S.C. § 371 under PCT/US15/57591, filed Oct. 27, 2015, which claims benefit of U.S. Provisional Application No. 62/069,057, filed Oct. 27, 2014, which are hereby incorporated herein by reference in their entireties.

TECHNICAL FIELD

The present application generally relates to compositions and methods comprising natural killer (NK) cells. More particularly, the application relates to the in vivo, ex vivo, or in vitro stimulation and expansion of endogenous natural killer (NK) cells, which are capable of attacking and killing cancer cells, virally infected cells and certain immune cells.

BACKGROUND

Hematopoietic stem cell transplantation (HSCT) from genotypically HLA-matched siblings has improved long-term survival in patients with hematologic cancer malignancies and marrow failure syndromes. Every year, more than 10,000 Americans get life-threatening diseases for which the only hope of a cure is a bone marrow transplant from an unrelated donor or cord blood unit. However, more than 70% of patients who could benefit from an allogeneic stem cell transplant do not have a matched sibling donor. These circumstances delay treatment, making it necessary to resort to less than optimal use of a partially mismatched donor, which eventually leads to increased incidence of graft-versus-host disease (GVHD), graft failure, and relapse, all of which dramatically decrease patient survival.

Additional limitations are posed by the duration and the costly financial, mental, and health burdens of the transplant process. Thus, the application of HSCT from an unrelated donor is limited to younger, healthier patients with appropriate socioeconomic support that can endure the process.

Further challenges are posed by the high rate of relapse due to the inability to eradicate residual cancer cells. Although HSCT is considered to be curative, cancer relapse rates are staggering. Thus, novel, more targeted immuno-therapies are needed that would be more effective, preferably without the need for a matched donor. Donor lymphocyte infusion (DLI), for the treatment of acute myeloid leukemia (AML) relapse after HSCT was introduced in 1990s. This approach consisted of the administration of lymphocytes from the original donor to the AML patient with relapsed disease. Yet, clinical benefits were limited and observed only in a minority of patients with smaller tumor burdens, and T cell mediated GVHD often further worsened the outcomes.

There is a great need for new and improved methodologies aimed at increasing NK cell numbers.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

SUMMARY

Disclosed herein are methods for improved technologies for enhancing the activity of natural killer (NK) cells. In certain embodiments the methods disclosed herein result in increased number of NK cells. In certain embodiments the methods disclosed herein result in NK cells having improved activity. In certain embodiments, the methods disclosed herein result in increased numbers of NK cells with improved activity.

Disclosed herein are methods for increasing the number of NK cells, comprising, contacting at least one NK cell with at least one NK-stimulating exosome comprising one or more stimulatory peptides present in an exosome membrane. The exosomes can be an extracellular product of exosome-secreting cells produced in vitro. In some cases, the exosomes are secreted from feeder cells. In some aspects, the one or more stimulatory peptides present in the exosome membrane may comprise 4-1BBL, IL-2, IL-12, IL-18, IL-21, MICA/B, ULBP2, ICAM-1, 2B4, BCM1/SLAMF2, CD155, CD112, CCR7 and/or other homing receptor, DAP12, DAP10 and/or other adaptor proteins. In some cases, the exosome membrane does not contain IL-15. In some aspects, the one or more stimulatory peptides present in the exosome membrane comprises 4-1BBL and IL-21. The stimulatory peptides may also be coupled to one or more membrane-inserting peptides. The membrane-inserting peptide may comprise segments of CD4 or an IgG with affinity for a lipid bilayer. Alternatively, the membrane-inserting peptide may comprise human Fc, GPI, trans-membrane T-cell receptor, or pHLIP. The one or more stimulatory peptides coupled to one or more membrane-inserting peptides may comprise a fusion protein encoded by recombinant DNA.

In some embodiments, the exosomes are produced by feeder cells in co-culture with the NK cells. One disadvantage associated with current co-culture methods is the likelihood of contamination. However, since no direct cell-cell contact is required between the feeder cells and the NK cells with the disclosed methods, the cells can be separated by a membrane sized to allow passage of exosomes. Therefore, also disclosed herein is a bioreactor comprising feeder cells and NK cells separated by a membrane sized to allow passage of exosomes. Such bioreactors may be designed with multiple compartments separated by molecular porous membranes or a hollow fiber type with molecular porous membranes that allow exosomes to traverse but not cells. Such bioreactor designs could be incorporated as part of a larger device or system for cell activation, cell growth or cell processing.

The exosomes used herein may be produced by cell lines engineered for improved expression of exosomes. In some cases, the cell line is a leukemia cell line, such as K562 cells. In some cases, the cell line has been engineered to express the one or more stimulatory peptides, such as 4-1BBL and IL-21. Therefore, in some embodiments, the cell line comprises K562-mb21-41BBL. In some embodiments the exosomes are produced from PBMCs. In some cases, the cell line is Epstein-Barr virus-infected such as EBV-LCL cells or Cytomegalovirus-infected or co-infected.

NK cells may be contacted with, or exposed to, NK-stimulating exosomes in vitro, in vivo, or ex vivo. For example, the NK cells may be contacted with NK-stimulating exosomes in an allogeneic transplant procedure, a haploidentical transplant procedure or an in vivo immunotherapy procedure. In some aspects, the use of NK-stimulating exosomes in allogeneic transplants, haploidentical transplants or in vivo immunotherapy does not cause graft-versus-host-disease (GVHD).

In some aspects, the NK cells are present in a population of unselected peripheral blood mononuclear cells (PBMCs). In some embodiments, whole blood or PBMCs isolated from a subject are contacted with the disclosed exosomes ex vivo to expand NK cells within the PBMCs. In some embodiments, the exosomes are contacted with NK cells derived from induced pluripotent stem cells (IPSCs), PBMCs, cord blood, isolated NK cell progenitors, or any combination thereof. Once contacted, the whole blood, PBMCs, expanded NK cells, isolated NK cells, or NK cell product depleted of other lymphoid cell types can be transfused back into the subject. Either stimulation with exosomes of NK cells or NK cell containing cell populations for activation or expansion can be performed in standard tissue culture plates or flasks, closed bag systems (eg CliniMacs Prodigy system by Miltenyi), hollow fiber devices (Quantum Cell Expansion System by TerumoBCT), G-Rex flask (Wilson Wolf), or other devices.

Disclosed herein are methods for treating cells susceptible to NK-mediated lysis, comprising administering to the cells an effective amount of a composition comprising contacted NK cells. The contacted NK cells may be produced by a method comprising contacting at least one NK cell with at least one NK-stimulating exosome comprising one or more stimulatory peptides present in an exosome membrane, wherein the exosome is an extracellular product of exosome-secreting cells. In some aspects, the cells susceptible to NK mediated lysis may be infected with a virus. The cells susceptible to NK mediated lysis may comprise malignant cells such as those associated with cancer, including but not limited to AML, breast, bladder, colon and rectum, kidney, lung, prostate, thyroid, and uterine cancer.

Disclosed are methods for lowering the risk of relapse after stem cell transplantation, and methods for adjuvant therapy comprising administering an effective amount of a composition comprising contacted NK cells, wherein the contacted NK cells are produced by a method comprising contacting at least one NK cell with at least one NK-stimulating exosome comprising one or more stimulatory peptides present in an exosome membrane, wherein the exosome is an extracellular product of exosome-secreting cells.

Disclosed are methods of producing NK cell-stimulating exosomes, comprising, embedding one or more stimulatory peptides in the membrane of an exosome. The stimulatory peptides may comprise 4-1BBL, IL-2, IL-12, IL-18, IL-21, MICA/B, ULBP2, ICAM-1, 2B4, BCM1/SLAMF2, CD155, CD112, CCR7 and/or other homing receptor, DAP12, DAP10 and/or other adaptor proteins r. The stimulatory peptides may optionally be coupled to a membrane-inserting peptide. The membrane-inserting peptide may comprise CD4 or an IgG with affinity for a lipid bilayer. Alternatively, the membrane-inserting peptide may further comprise human Fc, GPI, trans-membrane T-cell receptor, or pHLIP. The one or more stimulatory peptides coupled to one or more membrane-inserting peptides may comprise a fusion protein encoded by recombinant DNA. In some aspects, the NK cell-stimulating exosomes may be from cell lines engineered for improved expression of exosomes, including but not limited to, cell line K562-mb15-41BBL or cell line K562-mb21-41BBL.

Disclosed are methods for treating cancer, comprising, administering an effective amount of a composition comprising NK-stimulating exosomes comprising one or more stimulatory peptides. The use of NK stimulating exosomes may comprise administering the NK stimulating exosomes to a subject. In some aspects, the use of NK stimulating exosomes may comprise contacting NK stimulating exosomes to NK cells ex vivo to obtain a contacted NK cell population and administering the contacted NK cell population to a subject.

Disclosed are compositions, comprising, NK stimulating exosomes comprising one or more stimulatory peptides. The stimulatory peptides may comprise 4-1BBL, IL-2, IL-12, IL-18, IL-21, MICA/B, ULBP2, ICAM-1, 2B4, BCM1/SLAMF2, CD155, CD112, CCR7 and/or other homing receptor, DAP12, DAP10 and/or other adaptor proteins. The stimulatory peptides may optionally be coupled to one or more membrane-inserting peptides. The membrane-inserting peptides may comprise segments of CD4 or an IgG with affinity for a lipid bilayer. Alternatively, the membrane-inserting peptide may further comprise human Fc, GPI, trans-membrane T-cell receptor, or pHLIP. The one or more stimulatory peptides coupled to a membrane-inserting peptide may comprise a fusion protein encoded by recombinant or transgenic DNA. The NK stimulating exosomes may be from cell lines engineered for improved expression or production of exosomes, including but not limited to cell line K562-mb21-41BBL or derivatives. In some aspects, the composition may further comprise a pharmaceutical carrier. Disclosed are methods of treating cancer comprising administering to a subject an effective amount of a composition for enhancing NK cells wherein the composition comprises NK cells modified with at least one NK-stimulating exosome comprising one or more stimulatory peptides present in an exosome membrane. Disclosed are methods of treating cancer comprising administering to a subject an effective amount of a composition for enhancing NK cells wherein the composition comprises NK cells modified with at least one NK-stimulating exosome comprising one or more stimulatory peptides present in an exosome membrane wherein the stimulatory peptides comprise 4-1BBL, IL-2, IL-12, IL-18, IL-21, MICA/B, ULBP2, ICAM-1, 2B4, BCM1/SLAMF2, CD155, CD112, CCR7 and/or other homing receptor, DAP12, DAP10 and/or other adaptor proteins. Disclosed are methods of treating cancer comprising administering to a subject an effective amount of a composition for enhancing NK cells wherein the composition comprises NK cells modified with at least one NK-stimulating exosome comprising one or more stimulatory peptides present in an exosome membrane and wherein the composition further comprises membrane-inserting peptide. Disclosed are methods of expanding NK cells comprising administering to a cell population an effective amount of a composition comprising at least one NK-stimulating exosome comprising one or more stimulatory peptides present in an exosome membrane. Disclosed are methods of expanding NK cells comprising administering to a cell population an effective amount of a composition comprising at least one NK-stimulating exosome comprising one or more stimulatory peptides present in an exosome membrane, wherein the stimulatory peptides comprise 4-1BBL, IL-2, IL-12, IL-18, IL-21, MICA/B, ULBP2, ICAM-1, 2B4, BCM1/SLAMF2, CD155, CD112, CCR7 and/or other homing receptor, DAP12, DAP10 and/or other adaptor proteins. Disclosed are methods of expanding NK cells comprising administering to a subject an effective amount of a composition for enhancing NK cells wherein the composition comprises NK cells modified with at least one NK-stimulating exosome comprising one or more stimulatory peptides present in an exosome membrane and wherein the composition further comprises membrane-inserting peptide. Disclosed are methods of expanding NK cells comprising administering to a subject an effective amount of a composition for enhancing NK cells wherein the composition comprises NK cells modified with at least one NK-stimulating exosome comprising one or more stimulatory peptides present in an exosome membrane and wherein the composition further comprises membrane-inserting peptide, wherein the membrane self-inserting peptide comprises human Fc, GPI, transmembrane T-cell receptor, or pHLIP Disclosed are methods of modulating the immune system comprising administering to a subject an effective amount of a composition for enhancing NK cells wherein the composition comprises NK cells modified with at least one NK-stimulating exosome comprising one or more stimulatory peptides present in an exosome membrane and wherein the composition further comprises membrane-inserting peptide.

Therefore, also disclosed is a pharmaceutical composition comprising the disclosed exosomes in a pharmaceutically acceptable vehicle. For example, the exosomes can be formulated as an injectable with suitable carrier chemical components.

The disclosed NK-stimulating exosomes and/or contacted NK cells can be administered to a subject alone or in combination with a cancer immunotherapy, including, but not limited to, therapeutic antibodies, cancer vaccines, immune checkpoint inhibitors, and adoptive cell therapy (ACT).

Disclosed herein are methods for stimulating NK cells that involves contacting the NK cell with at least one NK-stimulating exosome wherein the NK-stimulating exosome is loaded with an NK-stimulating functional nucleic acid, such as siRNA or miRNA. For example, in some cases, the NK-stimulating functional nucleic acid is an inhibitor (e.g., antagonists, expression inhibitor, or silencer) of A2AR, P2YR, or a combination thereof.

DESCRIPTION OF DRAWINGS

The accompanying drawings, which are incorporated in and constitute a part of this specification, illustrate several embodiments of the disclosed method and compositions and together with the description, serve to explain the principles of the disclosed method and compositions.

FIGS. 3A and 3B show exosomes isolated from culture of K562-mb21-41bbl cells stimulate specific expansion of NK cells from unselected PBMCs. Unselected PBMCs were cultured with exosomes isolated from culture of K562-mb21-41bbl cells at 35 ng/mL of total protein. After an initial lag, NK cells expanded exponentially by an average of 270 fold over 20 days (FIG. 3A) and rose in relative abundance of total lymphocytes to 74% (FIG. 3B). All cultures were grown in duplicate and the markers represent the average with the error bars representing the standard deviation.

DETAILED DESCRIPTION

Figure 1:
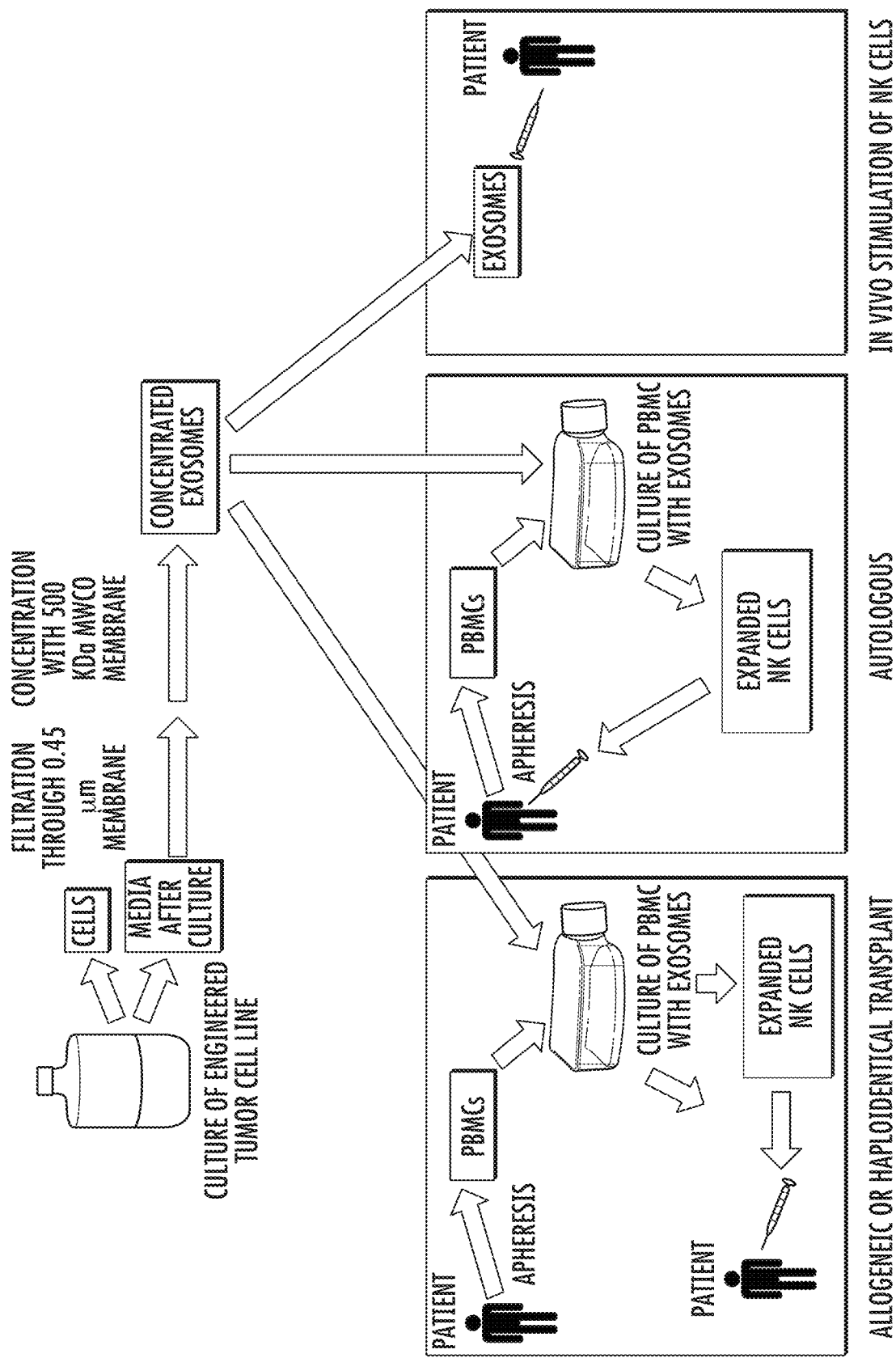
FIG. 1 is a depiction of how exosomes isolated from a culture of K562-mb21-41BBL cells containing stimulatory ligands (IL-21 and 41BBL) can be used to stimulate NK cells in allogeneic, haploidentical, autologous, and direct in vivo settings of cancer treatment.

The disclosed methods and compositions may be understood more readily by reference to the following detailed description of particular embodiments and the Example included therein and to the Figures and their previous and following description. All references cited herein including PCT/US2013/048678 are incorporated herein in their entirety.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

A significant portion of donor lymphocyte infusion mediated graft-versus-tumor (GVT) effect may be due to natural killer (NK) cells. The infusion of NK cells isolated from donor blood could produce beneficial GVT effects without causing GVHD. Preclinical and clinical data has shown effectiveness of NK cell infusions leading toward complete remission without any GVHD. Thus, NK cell infusion, in combination with autologous transplantation, or as a standalone treatment, offers an innovative, and potentially very effective, alternative for those patients who do not have a matched donor, experience relapse, or do not qualify for transplant.

Infusions of NK cells are a treatment option for patients with cancers susceptible to NK cell lysis, including blood cancers (such as acute myeloid leukemia or multiple myeloma) and several solid tumors (e.g. brain tumor, Ewing sarcoma and rhabdomyosarcoma) (Harada, Saijo et al. 2002; Ruggeri, Capanni et al. 2002; Miller, Soignier et al. 2005; Cho, Shook et al. 2010). Increased numbers of functional NK cells can also significantly enhance the efficacy of therapeutic antibodies used in treatment of several cancers, including lymphomas, colorectal cancer, lung cancer, and breast cancer, among others (Hatjiharissi, Xu et al. 2007; Triulzi, Vertuani et al. 2010; Houot, Kohrt et al. 2011; Tai, Horton et al. 2012). These types of personalized treatments are, however, very costly, with a typical antibody-containing regimen costing tens of thousands of dollars. Furthermore, the expected efficacy of existing methods is often not achieved due to the lack of immune cell engagement in immune compromised cancer patients (Dewan, Takada et al. 2009; Mamessier, Sylvain et al. 2011).

To be effective as a cancer treatment method, it is desirable to achieve a degree of NK cell expansion that reaches an effective therapeutic dose. Several studies have shown that NK cells proliferate in an in vitro culture exponentially and preferentially within a mixture of peripheral blood mononuclear cells (PBMC) when stimulated cytokines (such as IL-15 or IL-21) and ligands for activating receptors (such as 4-1BBL) expressed on the surface of stimulator cells (Imai, Iwamoto et al. 2005; Cho and Campana 2009; Lee, Verneris et al. 2010; Somanchi, Senyukov et al. 2011).

For cytokines IL-15 and IL-21, cross-presentation of membrane bound interleukin, as in normal dendritic cells, induces expansion of NK cells more potently than the soluble form of these cytokines. Moreover, under such stimulation conditions, only a low concentration of soluble IL-2 is required for NK cell survival, thus allowing for selective expansion of NK cells within a PBMC mixture without observable proliferation of T cells. The soluble form of IL-15 and IL-21 cytokines or high dose IL-2 stimulate more potently the proliferation of T cells than of NK cells. A previously published study by Campana and coworkers has shown that in an in vitro culture stimulation of NK cells with the K562 cell line having membrane bound IL-15 and 4-1BBL leads to a potent expansion of NK cells that is not observed with K562 cells expressing either of the molecules alone (Imai, Iwamoto et al. 2005; Fujisaki, Kakuda et al. 2009). However, NK cell expansion was limited to several divisions and the cells achieved senescence and stopped proliferating, coinciding with the observation of telomere shortening. In a follow-up study, stimulation with membrane bound IL-21 instead of IL-15 was found to stimulate continuous propagation of NK cells over countless generations allowing for continuous expansion of NK cells provided that the culture is periodically replenished with fresh stimulatory cells (Somanchi, Senyukov et al. 2011; Denman, Senyukov et al. 2012). While these methods allow for efficient in vitro NK cell expansion, the need for live feeder cells makes the methodology difficult to transfer to clinical settings that do not have large GMP facility and capability. Also, NK cells that are infused into the patient will likely stop dividing due to the lack of continued stimulation by the feeders. Furthermore, there is still a lack of information about the ability of in vitro cultured NK cells to function as intended when re-infused into a patient (Miller 2009). Currently IL-2 administration is the only FDA approved method of expansion of NK cells in vivo. IL-15 is currently being tested in a Phase I clinical trial as an alternative approach to IL-2 administration but based on preclinical findings it is still expected to have significant toxicity if administered systematically. Thus, both methods carry significant toxicities to patients and also induce proliferation of T-cells including regulatory T-cells leading to short persistence (on average less than 21 days) of NK cells.

A successful pilot trial showed that infusion of purified NK cells isolated from donor's blood is safe and can lead to complete remission of AML, with no GVHD. To reach a therapeutic dose, NK cells were expanded in vivo in lymphodepleted patients by daily administration of high dose IL-2. However, the intensive conditioning regimen required for lymphodepletion and the high doses of IL-2 used in this study resulted in significant toxicity and prolonged hospitalization, and in many cases, low in vivo expansion on NK cells. Moreover, systemic administration of IL-2 leads to proliferation of regulatory T cells that suppress the numbers and function of NK cells, thereby limiting their persistence and efficiency in the patient. Thus, alternative approaches for in vivo or ex vivo expansion of NK cells are needed.

The efficacy of NK cell immunotherapy is dependent on the dose of NK cells administered to the patient or reached after infusion through in vivo expansion. Currently available techniques are limited by their inability to achieve the level of NK cell expansion required to achieve a therapeutic effect in a patient. The lack of a simpler clinical expansion protocol is a major barrier to the progress and wide dissemination of NK cell-based immunotherapy. Current ex vivo expansion protocols use a combination of high dose cytokines with activating ligands expressed on leukemia-derived feeder/stimulator cell lines, posing a significant disadvantages for transfer to clinical settings in most centers and are not amenable for direct in vivo expansion. The use of particle technology, including exosomes, described herein eliminates the need for stimulator cells, thus simplifying the methodology and allowing direct and selective in vivo expansion.

Several groups have pursued a method to expand NK cells ex vivo. However, most of the currently developed ex vivo methods rely on co-culture systems of tumor cell lines and NK cells in the presence of high concentrations of various cytokines, mostly IL-2 (Reviewed in Cho and Campana 2009; Suck and Koh 2010). Cells used to trigger NK cell proliferation include irradiated autologous or allogeneic PBMCs, RPMI8866, HFWT, K562, K562-mb15-41BBL (K562 transfected with 4-1BBL and membrane-bound IL-15), K562-mb21-41BBL and EBV-LCL (Harada, Saijo et al. 2004; Imai, Iwamoto et al. 2005; Berg, Lundqvist et al. 2009; Fujisaki, Kakuda et al. 2009; Siegler, Meyer-Monard et al. 2010). Although expansion of NK cells can be significant with some of these cell lines (30-10,000 fold within 7-21 days), the use of feeder cells poses significant downsides for transfer into a clinical setting in most centers due to the requirement for a current Good Manufacturing Practice (cGMP) facility, which costs several million dollars (Reviewed in Cho and Campana 2009; Suck and Koh 2010). Furthermore, continuous culturing of feeder cells is costly and requires support of dedicated personnel. The National Institutes of Health (NIH) previously provided support in the manufacturing of cells for cellular therapy in the form of Production Assistance for Cellular Therapy (PACT). However, NK cells appear to lose their activity during cryopreservation (PACT workshop presentation). Thus, the storage and transport of expanded NK cells from the site of production to the transplant center is another obstacle in successful application of the therapy. An additional concern is the potential for infusion of live feeder cells and/or genetic material released from those transformed cells and culture components (e.g. fetal bovine serum) into a recipient patient.

Miltenyi Biotech has introduced an in vitro expansion kit that uses antibody-coated beads to crosslink activating NK cell receptors. However, this method requires the use of high concentration IL-2. While useful for laboratory applications, this method cannot be transferred to clinical settings because NK cells cultured using high concentrations of cytokines undergo rapid apoptosis after infusion due to cytokine withdrawal (Miller 2009).

Expansion of NK cells within PBMC has been reported with a high concentration of IL-2 and stimulation with anti-CD3 antibody for the first five days (Carlens, Gilljam et al. 2001; Alici, Sutlu et al. 2008). The overall NK cell expansion was close to 1000-fold, but most of the NK cells were actually NK-like T cells (Berg and Childs 2010). Thus, all of the methods pose significant difficulties for the transfer to clinical applications and none of the methods can be used in direct in vivo expansion.

Method for Increasing Number of NK Cells

Disclosed are methods for increasing the number of NK cells, comprising, contacting at least one NK cell with at least one NK-stimulating exosome comprising one or more stimulatory peptides present in an exosome membrane, wherein the exosome is an extracellular product of exosome-secreting cells.

Stimulatory Peptides

The stimulatory peptides suitable for use in the methods disclosed herein may include, but are not limited to, NK cell activating agents (i.e. stimulatory ligands) cytokines, or adhesion molecules. Examples of NK cell activating agents and stimulatory peptides include, but are not limited to, 41BBL, IL-2, IL-12, IL-21, IL-18, MICA, LFA-1, 2B4, BCM/SLAMF2, CCR7 and/or other homing receptors. Examples of cytokines include, but are not limited to, IL-2, IL-12, IL-21, and IL-18. Examples of adhesion molecules include, but are not limited to LFA-1, MICA, BCM/SLAMF2. In an aspect of the invention exosomes are vehicles used to carry stimulatory peptides. The stimulatory peptides may be present in the exosome membrane. While the stimulatory peptides are membrane bound, other therapeutic or diagnostic agents can be transported in the interior of the plasma membrane vesicle.

Membrane-Inserting Peptides Coupled to Stimulatory Peptides

Disclosed are methods for increasing the number of NK cells, comprising, contacting at least one NK cell with at least one NK-stimulating exosome comprising one or more stimulatory peptides present in an exosome membrane, wherein the exosome is an extracellular product of exosome-secreting cells, and wherein the one or more stimulatory peptides may be optionally coupled to one or more membrane-inserting peptides.

A membrane-inserting peptide may be a molecule that promotes insertion into a membrane. Membrane-inserting peptides may comprise segments of CD4 or an IgG with affinity for a lipid bilayer. In addition, alternative membrane-inserting peptides may comprise human Fc, GPI, transmembrane T-cell receptor, or pHLIP. The membrane self-inserting peptide may be any peptide known to insert into a cell membrane. Depending on the use of the membrane self-inserting peptide conjugate, certain membrane self-inserting peptides can be better choices than others. One of skill in the art would understand what membrane self-inserting peptide is ideal under different circumstances. For example, for in vivo use, pHLIP membrane self-inserting peptide may be suitable. pHLIP membrane self-inserting peptides insert into the membrane only under conditions of low pH. Therefore, pHLIP conjugates will not insert into cell membranes under normal physiological conditions. However, upon injection into a tumor environment, the pHLIP conjugate can insert into the cell membrane of tumor cells because the tumor environment is more acidic than normal physiological conditions. This insertion into the tumor environment allows for activation of NK cells in the area of the tumor. Using pHLIP thus prevents unwanted insertion into random cell membranes.

Membrane-inserting peptides may be coupled to one or more stimulatory peptides in a variety of ways and techniques for coupling peptides are well known in the art. A membrane-inserting peptide coupled to a stimulatory peptide can also be referred to as a membrane-inserting peptide conjugate. In some aspects, the one or more stimulatory peptides coupled to a membrane-inserting peptide may comprise a fusion protein encoded by recombinant DNA and such fusion-proteins may be produced in bacterial cells. In certain embodiments, fusion proteins may consist of one or more stimulatory peptides conjugated or coupled to a lipophilic molecule such as a hydrophobic peptide, GPI, or human Fc for anchoring into liposomes or cellular membranes (Hunt, Rath et al. 1997; Kueng, Leb et al. 2007; Paulick, Forstner et al. 2007; Paulick, Wise et al. 2007; Reshetnyak, Segala et al. 2007). cDNA vectors for these fusion proteins may be ligated into an expression plasmid, which allows expression in bacterial (*E. coli*), insect, or mammalian cells. In certain embodiments, cDNA vectors may be FLAG- or HIS-tagged. Bacterial cells may be transfected using standard CaCl transfection methods, such as that described in Sambrook et al., Molecular Cloning: A Laboratory Manual. 2nd ed. Cold Spring Harbor Laboratory Press (1989). Bacterial cells may also be cultured in LB media and cells can be harvested and lysed using a French Press. Proteins of interest can be purified from lysates by affinity chromatography. Palmitate-conjugated protein A and purified Fc fusion proteins can be conjugated as described in the literature by mixing 1:2 (w/w) at 4 degrees C. (see Kim & Peacock, Journal of Immunological Methods, 1993 Jan. 14; 158(1):57-65 and Liu et al., Journal of Immunology, 2007 Mar. 1; 178(5); 3301-3306). The conjugates may then be directly injected intratumorally or may be incorporated into liposomes.

Types of coupling and methods for coupling are known to those skilled in the art. As used herein, term "couple" refers to the membrane self-inserting peptide being conjugated, connected, or otherwise linked to another molecular entity such as a peptide or protein. For example, membrane-inserting peptides coupled to stimulatory peptides can be fusion proteins wherein the membrane-inserting peptide is coupled to another protein via a disulfide bond. Coupling or conjugating may mean that there is a chemical linkage between the membrane self-inserting peptide and the NK cell effector agent.

In some aspects, one or more stimulatory peptides may be coupled to membrane self-inserting peptides or GPI anchors for in situ self-assembly. For example, 41-BBL and IL-21 may be coupled to a pHLIP peptide which inserts itself into cellular membranes under acidic conditions, thereby allowing the anchoring of the stimulatory ligands into cells in the proximity of tumor. The stimulatory peptides 41BBL, IL-2, IL-12, IL-21, BCM/SLAMF2, CCR7 and/or other homing receptors may be produced in bacterial cells or purchased from commercially available sources and cDNA vectors for these proteins may optionally be ligated into pTriEX expression plasmid which allows expression in bacterial (*E. coli*), insect, or mammalian cells. The cDNA vector may code for expression of FLAG- or HIS-tag. Bacterial cells can be transfected using standard CaCl transfection methods and may be cultured on LB media. Cells can be harvested and lysed using a French press and proteins of interest may then be purified from lysates by affinity chromatography.

In some embodiments, pHLIP may be prepared by solid-phase peptide synthesis using 9-fluorenylmethyloxycarbonyl chemistry and the product may be purified on a C18 column by reverse-phase chromatography. pHLIP may then be conjugated to stimulatory human protein ligands by incubating with a crosslinker, such as benzophenone-4-iodoacetamide. After several washes, the conjugated pHLIP protein may be resuspended in media (saline, for example) and injected intratumorally or intravenously. Based on evidence from prior literature (Imai, Iwamoto et al. 2005; Liu, Breiter et al. 2007; Fujisaki, Kakuda et al. 2009; Somanchi, Senyukov et al. 2011; Denman, Senyukov et al. 2012) and presented in experimental results, interaction of NK cells with stimulatory ligands such as IL-21 and 41-BBL on the surface of such modified tumor cells may stimulate in situ NK cell expansion and trigger their cytotoxic response toward a tumor. This type of stimulatory approach can be used for treatments of solid tumors such as ovarian cancer where NK stimulatory ligands that insert in situ into tumor cells under acidic pH can be injected into intraperitoneal space of patients with low dose IL-2 alone or together with NK cells (Geller, Cooley et al. 2011). There is strong evidence that cytotoxic lymphocytes that express high levels of FCγIII R (CD16) such as NK cells are crucial for the efficacy of cancer therapy with therapeutic antibodies (Kute, Savage et al. 2009; Reim, Dombrowski et al. 2009; Mamessier, Sylvain et al. 2011). Thus, this approach can also be used in combination with therapeutic antibodies.

Functional Nucleic Acids

Disclosed herein are methods for modifying NK cell function (e.g., NK cell activation) comprising delivering a functional nucleic acid that modulates an NK cell function. The method can involve delivering the functional nucleic acid, including but not limited to siRNA, shRNA, or miRNA, to the NK cells by contacting the NK cell with at least one NK-stimulating exosome wherein the NK-stimulating exosome is loaded with the functional nucleic acid. For example, in some cases, the functional nucleic acid is intended to modulate the expression levels of A2AR, P2YR, or a combination thereof.

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, RNAi, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with mRNA or genomic DNA or they can interact with a polypeptide. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($K_d$) less than or equal to $10^{-6}$, $10^{-8}$, $10^{-10}$, or $10^{-12}$. A representative sample of methods and techniques which aid in the design and use of antisense molecules can be found in U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophylline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with $K_d$'s from the target molecule of less than $10^{-12}$ M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule (U.S. Pat. No. 5,543,293). It is preferred that the aptamer have a $K_d$ with the target molecule at least 10, 100, 1000, 10,000, or 100,000 fold lower than the $K_d$ with a background binding molecule. It is preferred when doing the comparison for a polypeptide for example, that the background molecule be a different polypeptide. Representative examples of how to make and use aptamers to bind a variety of different target molecules can be found in U.S. Pat. Nos. 5,476,766, 5,503, 978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, (U.S. Pat. Nos. 5,334,711, 5,436,330, 5,616,466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203; International Patent Application Nos. WO 9858058 by Ludwig and Sproat, WO 9858057 by Ludwig and Sproat, and WO 9718312 by Ludwig and Sproat) hairpin ribozymes (for example, U.S. Pat. Nos. 5,631,115, 5,646,031, 5,683,902, 5,712,384, 5,856,188, 5,866,701, 5,869,339, and 6,022,962), and tetrahymena ribozymes (for example, U.S. Pat. Nos. 5,595,873 and 5,652,107). There are also a number of ribozymes that are not found in natural systems, but which have been engineered to catalyze specific reactions de novo (for example, U.S. Pat. Nos. 5,580,967, 5,688,670, 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in U.S. Pat. Nos. 5,646,042, 5,693,535, 5,731,295, 5,811,300, 5,837,855, 5,869,253, 5,877,021, 5,877,022, 5,972,699, 5,972,704, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than $10^{-6}$, $10^{-8}$, $10^{-10}$, or $10^{-12}$. Representative examples of how to make and use triplex forming molecules to bind a variety of different target molecules can be found in U.S. Pat. Nos. 5,176,996, 5,645,985, 5,650,316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, Science 238:407-409 (1990)).

Similarly, eukaryotic EGS/RNAse P-directed cleavage of RNA can be utilized to cleave desired targets within eukaryotic cells. (Yuan et al., Proc. Natl. Acad. Sci. USA 89:8006-8010 (1992); WO 93/22434 by Yale; WO 95/24489 by Yale; Yuan and Altman, EMBO J 14:159-168 (1995), and Carrara et al., Proc. Natl. Acad. Sci. (USA) 92:2627-2631 (1995)). Representative examples of how to make and use EGS molecules to facilitate cleavage of a variety of different target molecules be found in U.S. Pat. Nos. 5,168,053, 5,624,824, 5,683,873, 5,728,521, 5,869,248, and 5,877,162.

Gene expression can also be effectively silenced in a highly specific manner through RNA interference (RNAi). This silencing was originally observed with the addition of double stranded RNA (dsRNA) (Fire, A., et al. (1998) Nature, 391:806-11; Napoli, C., et al. (1990) Plant Cell 2:279-89; Hannon, G. J. (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, S. M., et al. (2001) Genes Dev., 15:188-200; Bernstein, E., et al. (2001) Nature, 409:363-6; Hammond, S. M., et al. (2000) Nature, 404:293-6). In an ATP dependent step, the siRNAs become integrated into a multi-subunit protein complex, commonly known as the RNAi induced silencing complex (RISC), which guides the siRNAs to the target RNA sequence (Nykanen, A., et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, J., et al. (2002) Cell, 110:563-74). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer (Elbashir, S. M., et al. (2001) Nature, 411:494 498) (Ui-Tei, K., et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit.

The production of siRNA from a vector is more commonly done through the transcription of a short hairpin RNAs (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors. Disclosed herein are any shRNA designed as described above based on the sequences for the herein disclosed inflammatory mediators.

NK Cells

Disclosed are methods for increasing the number of NK cells, comprising, contacting at least one NK cell with at least one NK-stimulating exosome comprising one or more stimulatory peptides present in an exosome membrane, wherein the exosome is an extracellular product of exosome-secreting cells, and wherein the NK cells are present in a population of unselected peripheral blood mononuclear cells (PBMCs).

Human NK cells are a subset of peripheral blood lymphocytes defined by the expression of CD56 or CD16 and the absence of T cell receptor (CD3) (Ljunggren and Malmberg 2007; Woan and Reddy 2007). NK cells sense and kill target cells that lack major histocompatibility complex (MHC)-class I molecules. NK cell activating receptors include, among others, the natural cytotoxicity receptors (NKp30, NKp44 and NKp46), and lectin-like receptors NKG2D and DNAM-1. Their ligands are expressed on stressed, transformed, or infected cells but not on normal cells, making normal cells resistant to NK cell killing (Bottino, Castriconi et al. 2005; Gasser, Orsulic et al. 2005; Lanier 2005). NK cell activation is negatively regulated via inhibitory receptors, such as killer immunoglobin (Ig)-like receptors (KIRs), NKG2A/CD94, and leukocyte Ig-like receptor-1 (LIR-1). Engagement of one inhibitory receptor may be sufficient to prevent target lysis (Bryceson, Ljunggren et al. 2009). Hence NK cells efficiently target cells that express many stress-induced ligands, and few MHC class I ligands.

NK cells efficiently destroy tumor cells, stressed cells, and virally infected cells by a variety of different methods. The first is by directly engaging target cells, permeating their membranes, and then injecting a protein that cleaves and activates several apoptotic proteins, thereby initiating programmed cell death (apoptosis) of the targeted cell. The surface of an NK cell also contains protein ligands that can bind and activate receptors, such as the receptor for tumor-necrosis factor (TNF)-related apoptosis-inducing ligand (TRAIL), on target cells that turn on internal signals for apoptotic programmed cell death. When stimulated, NK cells can also secrete cytokines such as INFγ and TNFα that not only inhibit viruses and tumors, but also signal invasion to other immune cells. This broad and multimodal anticancer activity of NK cells make them of great interest to the medical field.

Because NK cells have a prominent role in the immune system, the ability to increase the number of NK cells provides treatment opportunities that were not possible or less effective with low numbers of NK cells.

Exosome

As disclosed herein, methods for increasing the number of NK cells, comprise, contacting at least one NK cell with at least one NK-stimulating exosome. The exosomes utilized herein comprise one or more stimulatory peptides present in the exosome membrane, and the exosome is an extracellular product of exosome-secreting cells. In certain embodiments, the exosome is produced by cell lines engineered for improved formation or release of exosomes; such cell lines include, but are not limited to, cell line K562-mb15-41 BBL or cell line K562-mb21-41BBL. Exosomes are natural vehicles secreted by many different types of cells and are found in various bodily fluids (Immune modulation of T-cell and NK (natural killer) cell activities by TEXs (tumour-derived exosomes) Whiteside T L, Biochem Soc Trans. 2013 Feb. 1; 41(1):245-51). The secretion of exosomes works by a highly regulated process and the particles produced are between 30 to 100 nm in size. Exosomes are comprised of lipids and proteins and the identity of the proteins found in a particular exosome is dependent on the cell(s) that produced them. The identity and composition of proteins found in a particular exosome determine how the exosome signals, influences, and interacts with other cells. Exosomes have been characterized to modulate immune cells and tumor cells and can be used to manipulate the biological activities of immune cells and tumor cells.

The smaller size of the exosomes will likely increase the diffusion of exosomes through physiological barriers and the biodistribution of exosomes compared to other larger sized plasma membrane particles. Further, because of the smaller size of the exosomes, intravenous injections of exosomes are possible, which may improve NK cell expansion and biodistribution through the circulatory system.

In some cases, the exosomes are from 30 to 100 nm in diameter.

Use of Exosome

Disclosed are methods for increasing the number of NK cells, comprising, contacting at least one NK cell with at least one NK-stimulating exosome comprising one or more stimulatory peptides present in an exosome membrane, wherein the exosome is an extracellular product of exosome-secreting cells, and wherein the NK cells are contacted with NK-stimulating exosomes in vitro, in vivo, or ex vivo. The NK cells can be contacted to NK-stimulating exosomes in an allogeneic transplant procedure, a haploidentical transplant procedure or an in vivo immunotherapy procedure. In some aspects, the use of NK-stimulating exosomes in allogeneic transplants, haploidentical transplants or in vivo immunotherapy does not cause graft-versus-host-disease (GVHD).

Methods of Treatment

Disclosed are methods for treating cells susceptible to NK mediated lysis, comprising administering an effective amount of a composition comprising contacted NK cells, wherein the contacted NK cells are produced by a method comprising contacting at least one NK cell with at least one NK-stimulating exosome comprising one or more stimulatory peptides present in an exosome membrane, wherein the exosome is an extracellular product of exosome-secreting cells. In some aspects, the cells susceptible to NK mediated lysis may be infected with a virus. The cells susceptible to NK mediated lysis may comprise AML breast, bladder, colon and rectum, kidney, lung, prostate, thyroid, and uterine cancer Disclosed are methods for lowering the risk of relapse after stem cell transplantation, and providing adjuvant therapy, comprising administering an effective amount of a composition comprising contacted NK cells, wherein the contacted NK cells are produced by a method comprising contacting at least one NK cell with at least one NK-stimulating exosome comprising one or more stimulatory peptides present in an exosome membrane, wherein the exosome is an extracellular product of exosome-secreting cells.

Expanded NK cells, compositions, and/or methods used to increase the number NK cells can be used as a treatment method for patients having cancers that are susceptible to NK cell mediated lysis as well as for patients who have undergone hematopoietic stem cell transplant. NK cell expanding compositions and methods can be used to increase the amount of cytotoxic NK cells after stem cell transplant for increased clearance of residual tumor cells and/or for relapse prevention. The NK cell-expanding compositions and methods can also be used to treat patients with viral infection.

NK cell expanding compositions and methods can be used as a post NK cell infusion treatment method to increase the numbers and in vivo persistence of cytotoxic NK cells for increased efficacy of NK cell therapy (i.e. number of patients that achieve remission and/or remain in remission).

NK cells with or without NK cell-expanding compositions will be used in combination with therapeutic antibodies for treatment of various cancers including, but not limited to, lymphomas, colorectal, lung, colon, head and neck, and breast cancers to increase the number of patients that respond to the therapeutic antibody therapy and achieve remission and/or remain in remission.

The methods of expanding NK cells are beneficial for treating cancer, treating viral infections, studying NK cells, treating multiple sclerosis, immune surveillance, and treating graft versus host disease. Any NK cell related disorder can be treated or affected by the expansion of NK cells. For example, diseases such as multiple sclerosis that are known for having an increase in activated T cells can be treated with the disclosed compositions because these compositions cause an expansion of NK cells that target and kill activated T cells. Thus, the disclosed compositions can be used to decrease activated T cells.

Method of Producing Exosomes

Disclosed are methods of producing NK cell-stimulating exosomes, comprising, embedding one or more stimulatory peptides in the membrane of an exosome. The stimulatory peptides may comprise 4-1BBL, IL-2, IL-12, IL-18, IL-21, MICA/B, ULBP2, ICAM-1, 2B4, BCM1/SLAMF2, CD155, CD112, CCR7 and/or other homing receptor, DAP12, DAP10 and/or other adaptor proteins. The stimulatory peptides can optionally be coupled to one or more membrane-inserting peptides. The membrane-inserting peptides may comprise CD4 or an IgG with affinity for a lipid bilayer. In addition, alternative membrane-inserting peptides may comprise human Fc, GPI, trans-membrane T-cell receptor, or pHLIP. The one or more stimulatory peptides coupled to the one or more membrane-inserting peptide(s) may be comprise a fusion protein encoded by recombinant DNA. In some aspects, the NK cell-stimulating exosomes can be from cell lines engineered for improved expression of exosomes: for example, the NK cell-stimulating exosomes can be from cell line K562-mb21-41BBL.

Exosomes are natural vehicles secreted by many different types of cells and are found in various bodily fluids (Whiteside 2013). Exosomes are comprised of lipids and proteins and the identity of the proteins found in a particular exosome is dependent on the cell(s) that produced them. Thus, cell lines expressing stimulatory peptides and/or stimulatory peptides coupled to a membrane-inserting peptide can produce exosomes having one or more stimulatory peptides embedded in the membrane of the exosomes.

Exosomes can be prepared using any of the techniques known in the art. For example, exosomes secreted by cells may be isolated from cell culture media by filtration (FIG. 1). Common protocols for preparing exosomes can be used.

Methods of Treating Cancer and Exosome Composition

Disclosed are methods for treating cancer, comprising, administering an effective amount of a composition comprising NK-stimulating exosomes comprising one or more stimulatory peptides. The use of NK stimulating exosomes can comprise administering the NK stimulating exosomes to a subject (FIG. 1). In some aspects, the use of NK stimulating exosomes can comprise contacting NK stimulating exosomes to NK cells ex vivo to obtain a contacted NK cell population and administering the contacted NK cell population to a subject (FIG. 1).

Disclosed are compositions, comprising, NK stimulating exosomes comprising one or more stimulatory peptides. The one or more stimulatory peptides can comprise 4-1BBL, IL-2, IL-12, IL-18, IL-21, MICA, 2B4, BCM1/SLAMF2, CCR7 and/or other homing receptors. The stimulatory peptides can be optionally coupled to one ore more membrane-inserting peptides. The membrane-inserting peptide can comprise segments of CD4 or an IgG with affinity for a lipid bilayer. Alternatively, the membrane-inserting peptides may comprise human Fc, GPI, trans-membrane T-cell receptor, or pHLIP. The one or more stimulatory peptides coupled to a membrane-inserting peptide can be a fusion protein encoded by recombinant DNA. The NK stimulating exosomes can be from cell lines engineered for improved expression of exosomes. The NK stimulating exosomes can be from cell line K562-mb21-41BBL. In some aspects, the composition may further comprise a pharmaceutical carrier.

Treating cancer with compositions comprising NK stimulating exosomes comprising one or more stimulatory peptides can occur due to the expansion or increase in the number of NK cells in the presence of these compositions. The expansion of NK cells leads to more NK cells able to target and kill tumor cells, thus reducing tumor cells and ultimately treating cancer or preventing relapse.

The compositions disclosed herein comprising NK stimulating exosomes comprising one or more stimulatory peptides can provide a preventative effect. NK cells are known to provide immunosurveillance. Therefore, administering a composition that results in expansion of NK cells allows for more NK cells to provide immunosurveillance and to target and kill pre-cancerous cells before cancer occurs.

In some aspects, the use of NK stimulating exosomes can comprise administering the NK stimulating exosomes to a subject by direct injection of the NK stimulating exosomes to cause in vivo NK cell expansion.

In some aspects, the use of NK stimulating exosomes can include administering the disclosed compositions to a cell population in vitro or ex vivo and then administering those treated cells to a subject. For example, the composition comprising NK stimulating exosomes can be administered to NK cells from PBMCs isolated by apheresis from a donor, and the contacted NK cells can be infused into a patient in an allogeneic or haploidentical transplant procedure (FIG. 1). The composition can also be administered to NK cells from PBMCs isolated by apheresis from a patient, and the contacted NK cells can be infused into the patient (FIG. 1).

Administration

The disclosed compositions can be administered in vitro or in vivo. In some aspects, the methods include a combination of in vitro and in vivo administration. The compositions can be administered in vivo in a pharmaceutically acceptable carrier. As known to those skilled in the art, the term "pharmaceutically acceptable" includes materials that are not biologically or otherwise undesirable, i.e., the material can be administered to a subject, along with an exosome or membrane self-inserting peptide conjugate, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions disclosed herein may be administered orally, parenterally (e.g., intravenously), by intramuscular injection, by intraperitoneal injection, by intratumoral injection, transdermally, extracorporeally, topically or the like, including topical intranasal administration or administration by inhalant. As used herein, "topical intranasal administration" includes delivery of the compositions into the nose and nasal passages through one or both of the nares and can comprise delivery by a spraying mechanism or droplet mechanism, or through aerosolization of the plasma membrane vesicles. Administration of the compositions by inhalant may be through the nose or mouth via delivery by a spraying or droplet mechanism. Delivery may also be directly to any area of the respiratory system (e.g., lungs) via intubation. The exact amount of the compositions required will vary from subject to subject, depending on the species, age, weight and general condition of the subject, the severity of the disorder being treated, the particular composition used, its mode of administration and the like. An appropriate amount can be determined by one of ordinary skill in the art using only routine experimentation given the teachings herein.

Pharmaceutical Carrier

The compositions disclosed herein may be used therapeutically in combination with a pharmaceutically acceptable carrier.

Suitable carriers and their formulations are described, for example, in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers can be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Compositions for oral administration include powders or granules, suspensions or solutions in water or non-aqueous media, capsules, sachets, or tablets. Thickeners, flavorings, diluents, emulsifiers, dispersing aids or binders can be desirable.

Some of the compositions can potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Combination Treatments

Disclosed are methods of treating cancer, viral infections, multiple sclerosis and graft-versus-host disease comprising administering to a subject one of the disclosed compositions in combination with a known therapeutic for the disease or disorder being treated. For example, disclosed are methods of treating cancer comprising administering an effective amount of a composition comprising NK stimulating exosomes comprising one or more stimulatory peptides in combination with a known cancer therapeutic such as, but not limited to, a chemotherapeutic, immunotherapeutic, radiation therapy or pain therapeutic.

There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Thus far, mAbs have been the biggest success story for immunotherapy; the top three best-selling anticancer drugs in 2012 were mAbs. Among them is rituximab (Rituxan, Genentech), which binds to the CD20 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

Generating optimal "killer" CD8 T cell responses also requires T cell receptor activation plus co-stimulation, which can be provided through ligation of tumor necrosis factor receptor family members, including OX40 (CD134) and 4-1BB (CD137). OX40 is of particular interest as treatment with an activating (agonist) anti-OX40 mAb augments T cell differentiation and cytolytic function leading to enhanced anti-tumor immunity against a variety of tumors.

In some embodiments, the disclosed vaccine is used in combination with adoptive cell therapies (ACT), such as Chimeric Antigen Receptors (CAR), T Cell Receptors (TCR), and Tumor Infiltrating Lymphocytes (TIL).

The term "tumor infiltrating lymphocyte" or "TIL" refers to white blood cells that have left the bloodstream and migrated into a tumor. Expansion of lymphocytes, including tumor-infiltrating lymphocytes, such as T cells can be accomplished by any of a number of methods as are known in the art. For example, T cells can be rapidly expanded using non-specific T-cell receptor stimulation in the presence of feeder lymphocytes and interleukin-2 (IL-2), IL-7, IL-15, IL-21, or combinations thereof. The non-specific T-cell receptor stimulus can e.g. include around 30 ng/ml of OKT3, a mouse monoclonal anti-CD3 antibody (available from Ortho-McNeil®, Raritan, N.J. or Miltenyi Biotec, Bergisch Gladbach, Germany). Alternatively, T cells can be rapidly expanded by stimulation of peripheral blood mononuclear cells (PBMC) in vitro with one or more antigens (including antigenic portions thereof, such as epitope(s), or a cell of the cancer, which can be optionally expressed from a vector, such as an human leukocyte antigen A2 (HLA-A2) binding peptide, e.g., approximately 0.3 µM MART-1:26-35 (27 L) or gp100:209-217 (210M)), in the presence of a T-cell growth factor, such as around 200400 µl/ml, such as 300 1 U/ml IL-2 or IL-15, with IL-2 being preferred. The in vitro-induced T-cells are rapidly expanded by re-stimulation with the same antigen(s) of the cancer pulsed onto HLA-A2-expressing antigen-presenting cells. Alternatively, the T-cells can be re-stimulated with irradiated, autologous lymphocytes or with irradiated HLA-A2+ allogeneic lymphocytes and IL-2, for example. Specific tumor reactivity of the expanded TILs can be tested by any method known in the art, e.g., by measuring cytokine release (e.g., interferon-gamma) following co-culture with tumor cells. In one embodiment, the autologous ACT method comprises enriching cultured TILs for CD8+ T cells prior to rapid expansion of the cells. Following culture of the TILs in IL-2, the T cells are depleted of CD4+ cells and enriched for CD8+ cells using, for example, a CD8 microbead separation (e.g., using a CliniMACS<plus>CD8 microbead system (Miltenyi Biotec)). In some embodiments, a T-cell growth factor that promotes the growth and activation of the autologous T cells is administered to the mammal either concomitantly with the autologous T cells or subsequently to the autologous T cells. The T-cell growth factor can be any suitable growth factor that promotes the growth and activation of the autologous T-cells. Examples of suitable T-cell growth factors include interleukin (IL)-2, IL-7, IL-15, IL-12 and IL-21, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2.

Numerous anti-cancer drugs are also available for combination with the present method and compositions. The following is a non-exhaustive lists of anti-cancer (anti-neoplastic) drugs that can be used in conjunction with irradiation: Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Elformithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

In some aspects, the cancer therapeutic and the NK stimulating exosomes can be formulated in the same composition. In some aspects, the cancer therapeutic and the NK-stimulating exosomes can be formulated in different compositions.

The composition comprising NK stimulating exosomes comprising one or more stimulatory peptides and the cancer therapeutic can be administered simultaneously or at different times. In some aspects, the NK stimulating exosomes comprising one or more stimulatory peptides are administered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days before or after the known therapeutic for the disease or disorder being treated. In some aspects, the NK stimulating exosomes comprising one or more stimulatory peptides are administered 1, 2, 3, 4, 5, 6, 7, 8, 9, 10, 11, or 12 months before or after the known therapeutic for the disease or disorder being treated.

Devices

Disclosed are devices comprising NK stimulating exosomes comprising one or more stimulatory peptides. For example, a container used during apheresis can comprise NK stimulating exosomes comprising one or more stimulatory peptides. Thus, during apheresis the cells that pass through the container can be incubated or placed into contact with the NK stimulating exosomes allowing for stimulation of the NK cells and ultimately NK cell expansion.

Kits

The materials described above as well as other materials can be packaged together in any suitable combination as a kit useful for performing, or aiding in the performance of, the disclosed methods. It is useful if the kit components in a given kit are designed and adapted for use together in the disclosed method.

The disclosed kits can also include stimulatory peptides. The kits can further contain components for preparing NK stimulating exosomes.

Definitions

It must be noted that as used herein and in the appended claims, the singular forms "a", "an", and "the" include plural reference unless the context clearly dictates otherwise. Thus, for example, reference to "an exosome" includes a plurality of such exosomes, reference to "the stimulatory peptide" is a reference to one or more stimulatory peptides and equivalents thereof known to those skilled in the art, and so forth.

"Exosome" refers to a membrane vesicle that is produced by or secreted by live cells. The term does not include synthetic liposomes derived from free lipid components or plasma membrane vesicles formed by processing disrupted cellular lipid membranes. The term also includes microvesicles, epididimosomes, argosomes, exosome-like vesicles, promininosomes, dex, tex, archeosomes and oncosomes, so long as they are produced or secreted by a cell. In some embodiments, the vesicles are release from the cell when multivesicular bodies fuse with the plasma membrane. In some cases, the vesicles are released directly from the plasma membrane.

"NK-stimulating exosome" or "NK cell-stimulating exosome" or "NK stimulating exosome" refers to an exosome capable of stimulating the production or increase in numbers of NK cells and/or the enhancement of NK cell activity, including but not limited to enhancing homing/targeting to the target cell to be lysed by cytotoxic activity of NK cells. The "NK-stimulating exosome" or "NK cell-stimulating exosome" or "NK stimulating exosome" may comprise one or more stimulatory peptides.

"Plasma membrane vesicle" refers to a preparation of a plasma membrane from a cell or an artificially made plasma membrane or liposome.

"Membrane-inserting peptides" are peptides that are capable of inserting or anchoring to a cell membrane.

"Stimulatory peptide" refers to stimulatory ligands that bind to activating receptors present on the surface of NK cells. Stimulatory peptide also refers to an agent that causes proliferation, stimulation, adhesion to or activation of NK cells. Stimulatory peptides can be cytokines, adhesion molecules or NK cell activating agents. "Modulate" or "modulating" as used herein refers to an increase or decrease. Modulating results in any difference compared to normal function. For example, modulating the immune system refers to increasing or decreasing immune cells.

"Optional" or "optionally" means that the subsequently described event, circumstance, or material may or may not occur or be present, and that the description includes instances where the event, circumstance, or material occurs or is present and instances where it does not occur or is not present.

"Contacting" as used herein means bringing one or more entities into proximity such that the entities may exert an effect on each other. "Contacting" may or may not involve physical contact. "Contact", "contacted", "contacting" and versions thereof further include exposing to, affecting, via direct or indirect interaction wherein said effect may or may not be mediated by, in concert with, or a result of interactions that include, but are not limited to cellular or molecular interactions.

As used herein, the term "subject" refers to any organism to which the disclosed compositions can be administered, e.g., for experimental, diagnostic, and/or therapeutic purposes. Typical subjects include animals (e.g., mammals such as non-human primates, and humans; avians; domestic household or farm animals such as cats, dogs, sheep, goats, cattle, horses and pigs; laboratory animals such as mice, rats and guinea pigs; rabbits; fish; reptiles; zoo and wild animals). Typically, "subjects" are animals, including mammals such as humans and primates; and the like. Subjects can also refer to a cell or a cell line.

Ranges may be expressed herein as from "about" one particular value, and/or to "about" another particular value. When such a range is expressed, also specifically contemplated and considered disclosed is the range, from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a membrane self-inserting peptide conjugate is disclosed and discussed and a number of modifications that can be made to a number of molecules including the membrane self-inserting peptide conjugate are discussed, each and every combination and permutation of the membrane self-inserting peptide conjugate and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

EXAMPLES

Example 1: Expansion of NK Cells by Crude Exosome Preparations

Results

As demonstrated herein, expansion of NK cells can occur by using exosomes derived from culture of K562-mb21-41BBL stimulator cells. Cultures of K562-mb21-41BBL were selected for isolation of exosomes because these cells were reported to expand NK cells very robustly and do not require the isolation of NK cells from peripheral blood mononuclear cell (PBMC) mixture prior to culture initiation. Furthermore, the presence of stimulatory ligands 41BBL and mbIL21 can be easily tracked by antibody staining to confirm expression of these molecules on the feeder cells and their presence in isolated exosomes.

Figure 4:
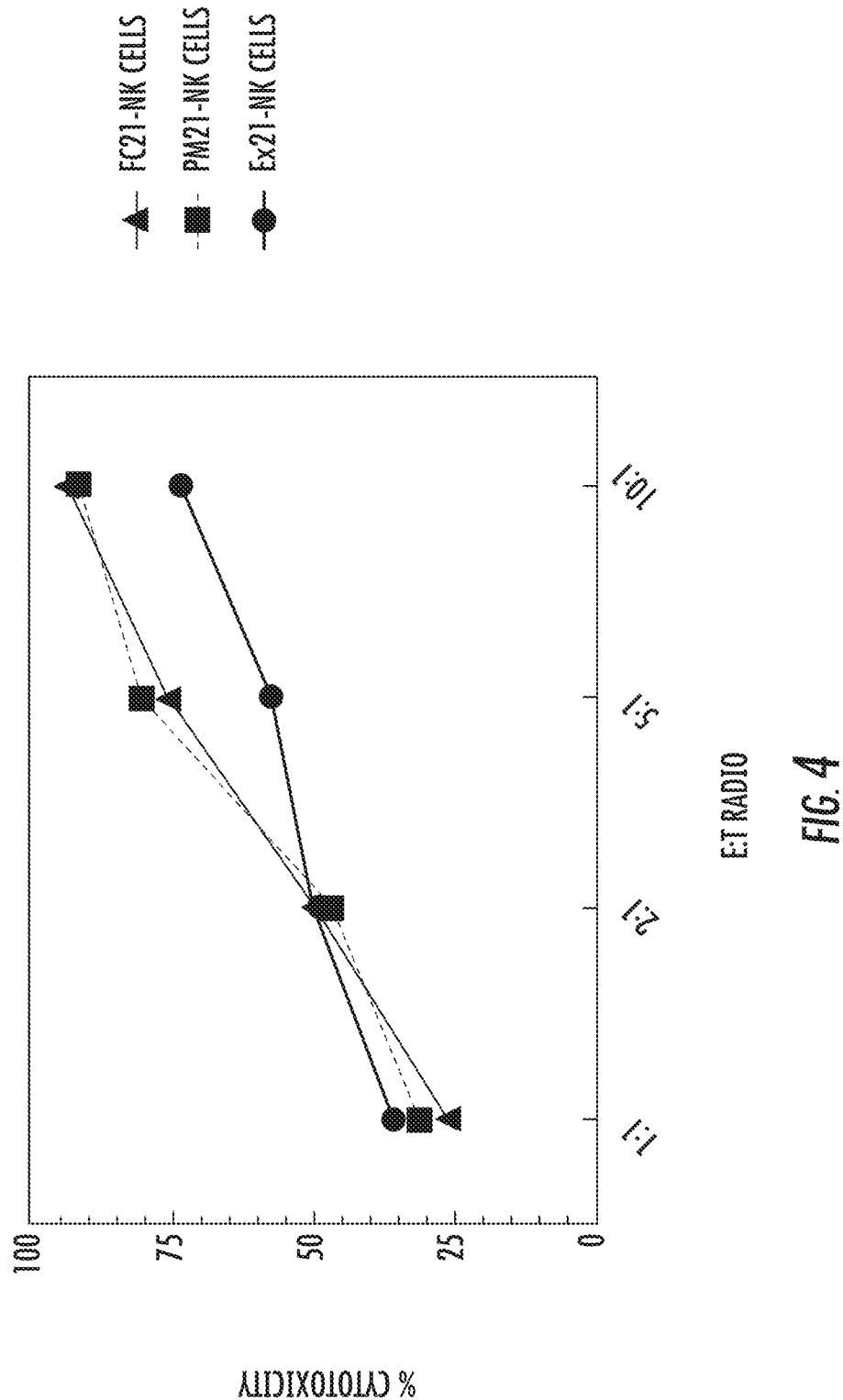
FIG. 4 shows NK cells stimulated and expanded with exosomes are cytotoxic against K562 cells. Unselected PBMCs were cultured with exosomes isolated from culture of K562-mb21-41bbl cells at 35 ng/mL of total protein and used for assaying cytotoxicity against K562 cells. The cytotoxicity of NK cells expanded with exosomes (Ex21-NK cells ●) are slightly lower compared to NK cells expanded with feeder cells (FC21-NK cells ▲) or with IL-21 bound plasma membrane particles (PM21-NK cells ■).

The present experiment was performed to test whether exosomes derived from a culture of stimulator cells supported expansion of NK-cells in a similar fashion as the stimulator cells. When PBMCs were exposed in culture to 50 U/mL of IL-2 and decreasing concentrations of crude exosomes isolated from culture media of K562-mb21-41BBL vesicles over 24 day period, the NK cells content in the PBMC mixture increased (FIG. 4). Concentrations of exosomes are indicated by the concentration of protein embedded in the exosomes. The crude exosome preparation likely contained certain substances from the culture that inhibited culture growth at higher concentrations of exosomes. But the crude exosome preparation was more effective when diluted. At a diluted concentration of exosomes used (50 μg/mL), an approximately 240-fold expansion of NK cells was observed, with the percentage of NK cells increasing to higher than 70%. Thus, this experiment indicates that NK cells can be selectively expanded within a PBMC mixture using exosomes embedded with stimulatory ligands without feeder cells.

Materials and Methods

The cell lines K562-mb15-41BBL and K562-mb21-41BBL (K562-clone9.mbIL21) were obtained from Dr. Dario Campana (St. Jude Children's Research Hospital) and Dr. Dean Lee (MD Anderson) respectively. The K562 cell lines used were purchased from the American Tissue Culture Collection (ATCC). The preparation of NK cell stimulating crude exosomes was performed according to the following. K562-mb21-41BBL cells were cultured in RPMI media supplemented with 10% FBS and the culture was scaled up to 1 L. After scale up, the K562-mb21-41 BBL culture was treated with 2 micromolar monensin. The media was recovered from cell culture by centrifugation at 1,000×g to pellet the cells. The recovered media was filtered using a 0.45 μm filter and then concentrated using a 100 KDa MWCO membrane. A BCA assay was used to determine the combined apparent protein concentration of the protein embedded in the exosomes and media.

PBMCs isolated from blood by Ficol-Paque density gradient were grown in SCGM Cell Gro media supplemented with 10% FBS, 50 U/mL of IL-2, and decreasing concentrations of exosomes. Cells were maintained at 37° C. in a humidified atmosphere with 5% $CO_2$. Starting on day 5, culture media was exchanged every other day by replacing half of the media with fresh media and exosomes removed by the culture media replacement were replaced. Cells were counted every other day and the culture content was checked.

Example 2: Characterization of Exosomes

NK cell stimulating exosomes were isolated from cultures of K562-mb21-41bbl cells. Cells were cultured to a density of approximately $1 \times 10^6$ cells/mL, washed, resuspended in serum free RPMI and treated with 2 μM monensin. Cells were removed by centrifugation at 1000×g for 10 minutes and then filtered through a 0.22 μm PES membrane. The filtered media was then concentrated by ultrafiltration using a 100,000 KDa MWCO membrane.

FIGS. 2A to 2D show characterization of exosomes isolated from culture of K562-mb21-41bbl cells. Exosomes were resuspended in PBS and characterized by Nanoparticle Tracking Analysis (NTA) of video microscopy with the NanoSight NS300 (Malvern). NTA determines particle size based on analysis of light scatter intensity and diffusion kinetics. Shown are a single frame light scatter image (FIG. 2A) and binned histogram of particle size distribution (FIG.

Figure 2B:
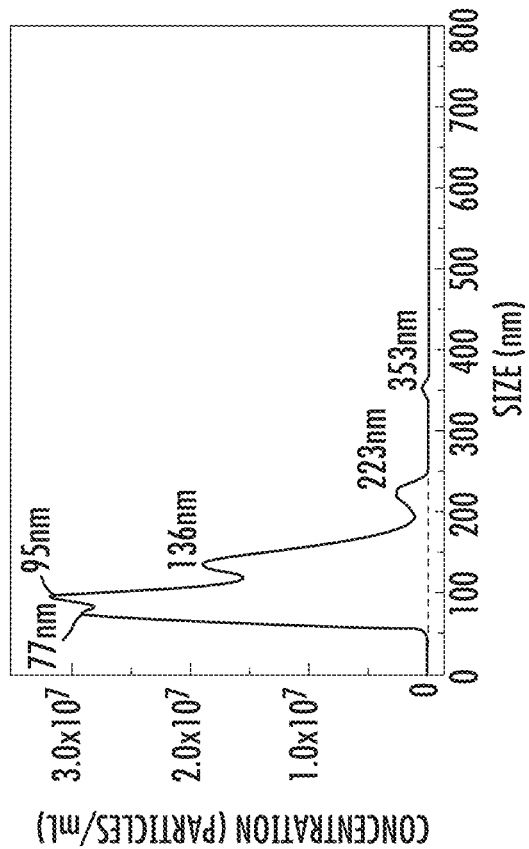
FIGS. 2A to 2D show characterization of exosomes isolated from culture of K562-mb21-41bbl cells. Exosomes were characterized by Nanoparticle Tracking Analysis of video microscopy with the NanoSight NS300 (Malvern). Shown are a single frame light scatter image (FIG. 2A) and binned histogram of particle size distribution (FIG. 2B). The presence of IL-21 was immunochemically confirmed by Western blot analysis with anti-IL21 ab (FIG. 2C). Analysis using anti IL-21 ab bound gold nanoparticle (GNP) (FIG. 2D) indicates the presence of IL-21 with exosome samples in which time dependent increase of dynamic light scatter intensity is observed with anti IL-21 ab bound GNP as compared to no increase for GNP bound with isotype control ab.
Figure 2A:
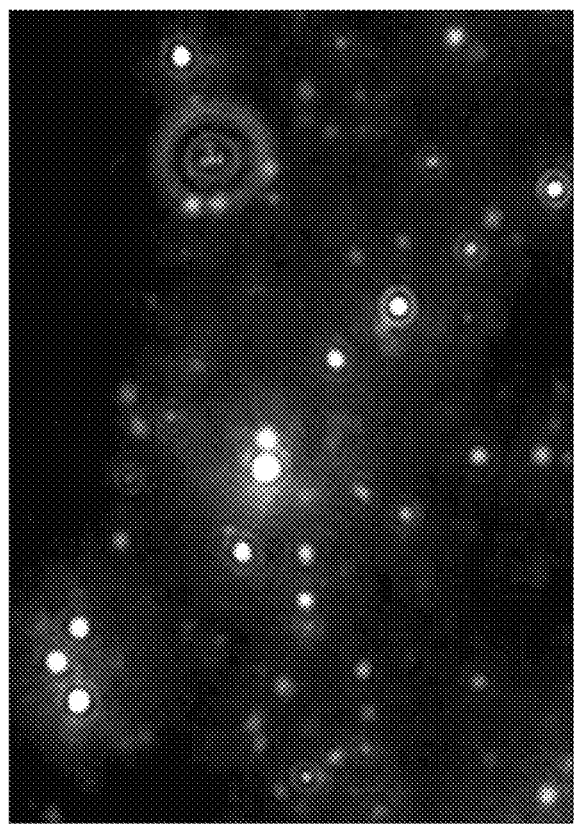
Figure 2D:
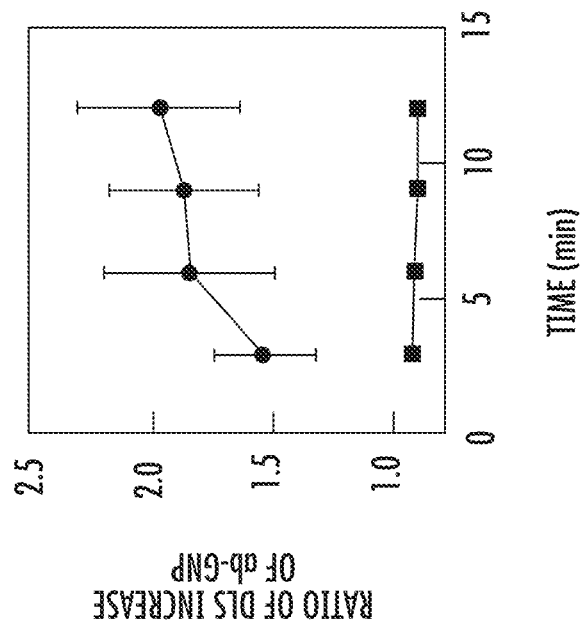
Figure 2C:
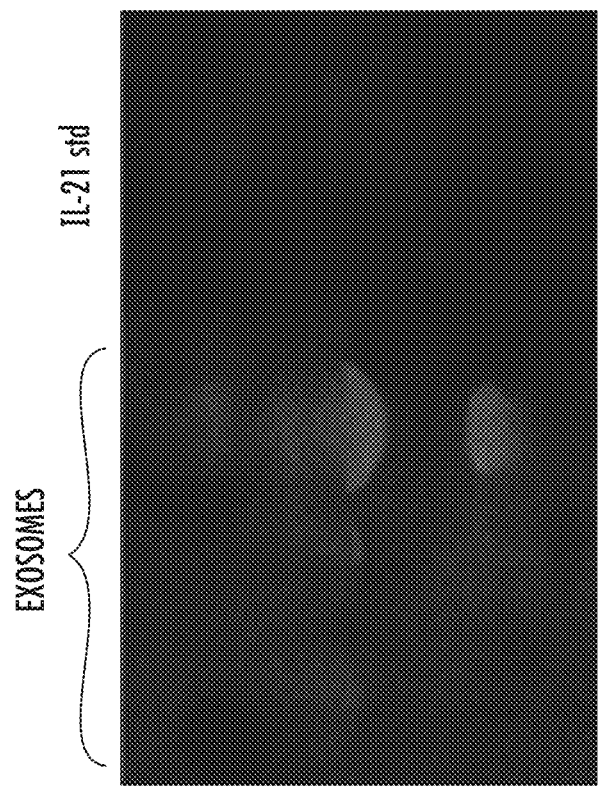

2B). The presence of IL-21 was immunochemically confirmed by Western blot analysis with anti-IL21 antibody (FIG. 2C). Analysis using anti-IL-21 antibody bound gold nanoparticle (GNP) (FIG. 2D) indicates the presence of IL-21 with exosome samples in which time dependent increase of dynamic light scatter intensity is observed with anti-IL-21 antibody bound GNP as compared to no increase for GNP bound with isotype control ab.

FIGS. 3A and 3B show exosomes isolated from culture of K562-mb21-41bbl cells stimulate specific expansion of NK cells from unselected PBMCs. Unselected PBMCs at an initial concentration of 100,000 NK cells/mL were cultured with exosomes isolated from culture of K562-mb21-41bbl cells at 35 ng/mL of total protein in SCGM media supplemented with 10% FBS. After an initial lag, NK cells expanded exponentially by an average of 270 fold over 20 days (FIG. 3A) and rose in relative abundance of total lymphocytes to 74% (FIG. 3B). Cultures were resuplemented with fresh media containing exosomes every other day. Exosomes isolated from cultures of regular non-transformed K562 not having transgenically expressed mbIL-21 and 4-1BBL did not induce expansion of NK cells. All cultures were grown in duplicate and the markers represent the average with the error bars representing the standard deviation.

NK cells expanded with exosomes were assayed for cytotoxicity against K562 CML tumor cells. K562 cells were pre-labeled with TFL4 dye. Target tumor cells were co-cultured at $0.5 \times 10^6$ K562 cells/mL with NK cells at indicated E:T ratios for 2 hours in 37° C., 5% $CO_2$ atmosphere. The cells were then centrifuged and resuspended in Annexin V labelling buffer containing Annexin V-FITC and incubated for 15 minutes at 4° C. The labeled cells were diluted to 250 µL and analyzed by flow cytometry on an Accuri instrument (BD Bioscience). FIG. 4 shows NK cells stimulated and expanded with exosomes are cytotoxic against K562 cells. Unselected PBMCs were cultured with exosomes isolated from culture of K562-mb21-41bbl cells at 35 ng/mL of total protein and used for assaying cytotoxicity against K562 cells. For comparison, NK cells were also expanded with K562-mb21-41bbl feeder cells and also with PM21-particles (200 µg/mL). The cytotoxicity of NK cells expanded with exosomes (Ex21-NK cells ●) are slightly lower compared to NK cells expanded with feeder cells (FC21-NK cells ▲) or with IL-21 bound plasma membrane particles (PM21-NK cells ■).

Figure 5A:
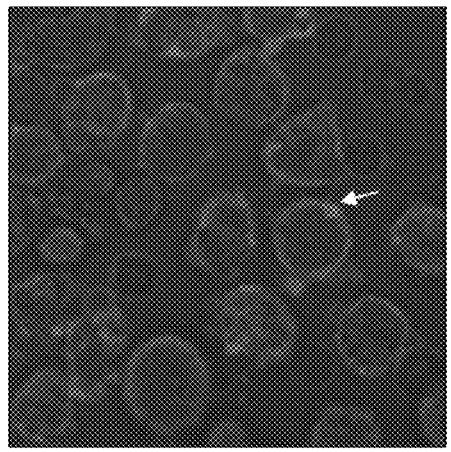
FIGS. 5A to 5E show exosomes produced by K562-mb21-41bbl in culture as feeder cells with PBMCS are uptaken by NK cells. K562-mb21-41bbl cells were externally labeled with AlexaFluor 647 (AF647), co-incubated with PBMCs, and then imaged over 18 hours by a 10 X objective. During the time of after minutes to about 1 hour (FIG. 5A), coalescence of the AF647 label is observed. After few hours (FIG. 5B), the formation of intracellular endosomes and multi-vesicular bodies are observed. Subsequently cell free exosomes are observed (FIGS. 5C and 5D). A sample from the co-culture being live imaged was obtained and stained with anti-CD3 and anti-CD56 and imaged by fluorescence confocal microscopy (FIG. 5E). The NK cells have uptaken or bind then AF647 label, while T cells preferentially do not. A wider area than shown was inspected for statistical validity and 10 slices along the Z-axis was imaged to discriminate intracellular and extracellular events. Arrows indicate the intracellular and extracellular particles or exosomes in culture.
Figure 5B:
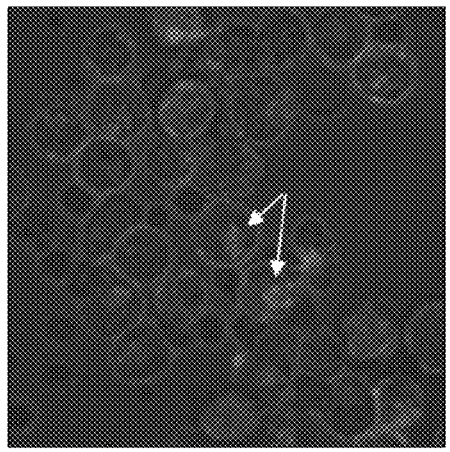
Figure 5C:
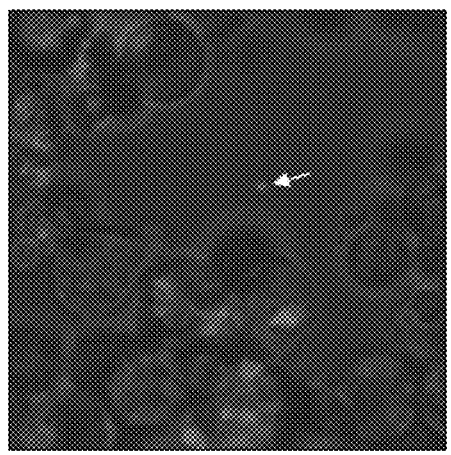
Figure 5D:
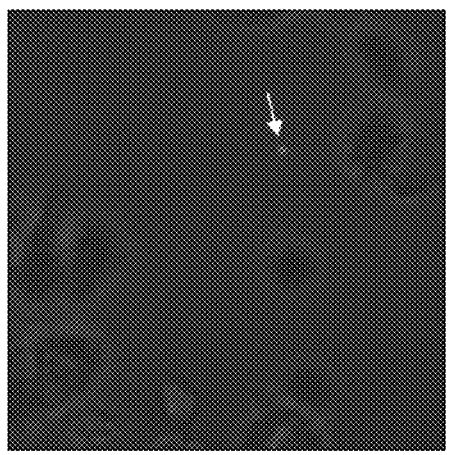
Figure 5E:
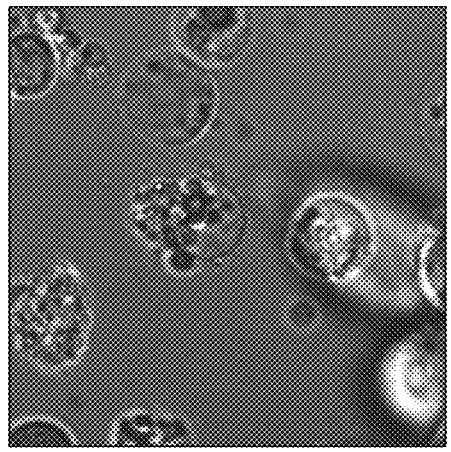

The presence of exosomes in co-culture of PBMCs together with K562-mb21-41bbl feeder cells was confirmed by video microscopy. FIGS. 5A to 5E show exosomes produced by K562-mb21-41bbl in culture as feeder cells with PBMCs (100,000 NK cells/mL) and feeder cells at a 10 fold excess, and then imaged over 18 hours by a 10 X objective on Perkin Elmer Ultraview Microscopy system fitted with a live cell imaging stage. During the time of after minutes to about 1 hour (FIG. 5A), coalescence of the AF647 label is observed. After few hours (FIG. 5B), the formation of intracellular endosomes and multi-vesicular bodies are observed. Subsequently cell free exosomes are observed (FIGS. 5C and 5D). A sample from the co-culture being live imaged was obtained and stained with anti-CD3 and anti-CD56 and imaged by fluorescence confocal microscopy (FIG. 5E). The NK cells have uptaken or bind then AF647 label, while T cells preferentially do not. A wider area than shown was inspected for statistical validity and 10 slices along the Z-axis was imaged to discriminate intracellular and extracellular events.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Those skilled in the art will recognize, or be able to ascertain using no more than routine experimentation, many equivalents to the specific embodiments of the method and compositions described herein. Such equivalents are intended to be encompassed by the following claims.

What is claimed is:

1. A method for increasing the number of NK cells, comprising, contacting at least one NK cell with at least one NK-stimulating exosome comprising one or more stimulatory peptides present in an exosome membrane, wherein the exosome is an extracellular product of an engineered exosomal secretory K562 cell line, wherein one or more stimulatory peptides comprise IL-21.

2. The method of claim 1, wherein the one or more stimulatory peptides are further comprise 4-1BBL, IL-2, IL-12, IL-18, MICA/B, ULBP2, ICAM-1, 2B4, BCM1/SLAMF2, CD155, CD112, CCR7, DAP12, or DAP10.

3. The method of claim 1, wherein the one or more stimulatory peptides are coupled to a membrane-inserting peptide.

4. The method of claim 3, wherein the membrane-inserting peptide comprises a fused peptide that is capable of membrane insertion, with affinity for a lipid bilayer, and wherein said fused peptide comprises a segment of IG4, CD4, or a combination thereof.

5. The method of claim 3, wherein the one or more stimulatory peptides coupled to a membrane-inserting peptide is a fusion protein encoded by recombinant DNA.

6. The method of claim 3, wherein the membrane-inserting peptide comprises human Fc, GPI, trans-membrane T-cell receptor, or pHLIP.

7. The method of claim 1, wherein the NK cells are present in a population of unselected peripheral blood mononuclear cells (PBMCs).

8. The method of claim 1, wherein the NK cells are contacted to the NK-stimulating exosomes in vitro, in vivo, or ex vivo.

9. The method of claim 8, wherein the NK cells are expanded in vivo in the intraperitoneal cavity, subcutaneously, or intravenously in the epidural space.

10. The method of claim 8, wherein the NK cells are contacted to the NK-stimulating exosomes in an allogeneic transplant procedure, a haploidentical transplant procedure, or an in vivo immunotherapy procedure.

11. The method of claim 10, wherein the method does not cause graft-versus-host-disease (GVHD) for allogeneic transplants, haploidentical transplants, or in vivo immunotherapy.

12. The method of claim 2, wherein one or more stimulatory peptides further comprises 4-1BBL.

* * * * *